US008058289B2

(12) United States Patent
Rueckle et al.

(10) Patent No.: US 8,058,289 B2
(45) Date of Patent: Nov. 15, 2011

(54) PYRIDINE METHYLENE AZOLIDINONES AND USE THEREOF PHOSPHOINOSITIDE INHIBITORS

(75) Inventors: Thomas Rueckle, Geneva (CH); Anna Quattropani, Geneva (CH); Vincent Pomel, Groisy (FR); Jerome Dorbais, Annecy (FR); David Covini, Neydens (FR); Alexander Bischoff, Smithtown, NY (US)

(73) Assignee: Merck Serono SA, Vaud (CH)

( * ) Notice: Subject to any disclaimer, the term of this patent is extended or adjusted under 35 U.S.C. 154(b) by 0 days.

(21) Appl. No.: 12/906,729

(22) Filed: Oct. 18, 2010

(65) Prior Publication Data
US 2011/0034458 A1    Feb. 10, 2011

Related U.S. Application Data

(62) Division of application No. 11/574,613, filed on Aug. 23, 2007, now Pat. No. 7,842,698.

(60) Provisional application No. 60/607,374, filed on Sep. 3, 2004.

(30) Foreign Application Priority Data

Sep. 3, 2004  (EP) .................................. 04104259

(51) Int. Cl.
*A61K 31/4355*   (2006.01)
*C07D 471/04*    (2006.01)
*A61P 29/00*     (2006.01)
*A61P 9/00*      (2006.01)
*A61P 25/28*     (2006.01)
*A61P 31/04*     (2006.01)
*A61P 31/12*     (2006.01)
*A61P 27/14*     (2006.01)
*A61P 37/08*     (2006.01)
*A61P 37/06*     (2006.01)
*A61P 1/18*      (2006.01)
*A61P 1/16*      (2006.01)
*A61P 7/02*      (2006.01)
*A61P 35/00*     (2006.01)

(52) U.S. Cl. ........................................ 514/302; 546/115
(58) Field of Classification Search .................. 546/115; 514/302
See application file for complete search history.

(56) References Cited

U.S. PATENT DOCUMENTS

| | | | |
|---|---|---|---|
| 2007/0021447 A1 | 1/2007 | Rueckle et al. | |
| 2007/0155776 A1 | 7/2007 | Betschmann et al. | |
| 2008/0306057 A1 | 12/2008 | Palmer et al. | |
| 2009/0028855 A1 | 1/2009 | Cheng et al. | |
| 2009/0042773 A1 | 2/2009 | Wetzker et al. | |
| 2009/0082357 A1 | 3/2009 | Fitch et al. | |
| 2009/0099172 A1 | 4/2009 | Cai et al. | |
| 2009/0306069 A1 | 12/2009 | Rueckle et al. | |
| 2010/0063066 A1* | 3/2010 | Buckmelter et al. | .......... 514/256 |

FOREIGN PATENT DOCUMENTS

| | | |
|---|---|---|
| WO | 2004 007491 | 1/2004 |
| WO | 2004 052373 | 6/2004 |
| WO | 2004 056820 | 7/2004 |

OTHER PUBLICATIONS

Shunsaku Shiotani, et al., "Furopyridines XXII' 1!. Elaboration of the C-Substituents Alpha to the Heteronitrogen Atom of Furo '2, 3-b!-, '3, 2-b!-, '2, 3-c!- and '3, 2-c! Pyridine", J. Heterocyclic Chem., vol. 34, XP 002313138, pp. 901-907, 1997.
Malvinder P. Shingh, et al., "Synthesis and Sequence-Specific DNA Binding of a Topoisomerase Inhibitory Analog of Hoechst 33258 Designed for Altered Base and Sequece Recognition", Chemical Research in Toxicology, vol. 5, No. 5, XP 002066288, pp. 597-607, 1992.
Kay M. Brummond, et al., "Solid-Phase Synthesis of BRL 49653", J. Org. Chem. vol. 64, pp. 1723-1726, 1999.
Lewis C. Cantley, "The Phosphoinoisitide 3-Kinase Pathway", Science, vol. 296, pp. 1655-1657, 2002.
M. P. Cava, et al., "Pyridine Derivatives. III. The Rearrangement of Some Simple 3-Halopyridine-N-Oxides", J. Org. Chem., vol. 23, pp. 1616-1617, 1958.
Jin Soon Cha, et al., "Exceptionally Facile Reduction of Acid Chlorides to Aldehydes by Sodium Tri-Tert-Butoxyaluminohydride", J. Org. Chem., vol. 58, No. 17, pp. 4732-4734, 1993.
J. D. Fraser, et al., "Regulation of Interleukin-2 Gene Enhancer Activity", Science, vol. 251, pp. 313-316, 1991.
David A. Fruman, et al., "Phosphoinositide Kinases", Annu. Rev. Biochem. vol. 67, pp. 481-507, 1998.
Graig Gerard, eta l., "Chemokines and Disease", Nature Immunology, vol. 2, No. 2, pp. 108-115, 2001.
Steven Grant, "Targeted Therapies in Cancer-Second International Congress", Idrugs, vol. 6, No. 10, pp. 946-948, 2003.
Emilio Hirsch, et al., "Central Role for G Protein-Coupled Phosphoinositide 3-Kinase γ in Inflammation", Science, vol. 287, pp. 1049-1053, 2000.
Emilio Hirsch, et al., "Resistance to Thromboembolism in PI3Kγ-Deficient Mice", The Faseb Journal, vol. 15, No. 11, pp. 2019-2021, 2001.
Roy Katso, et al., "Cellular Function of Phosphoinositide 3 Kinases: Implications for Development, Immunity, Homeostasis, and Cancer", Annu. Rev. Cell. Dev. Biol., vol. 17, pp. 617-675, 2001.

(Continued)

*Primary Examiner* — Susanna Moore
*Assistant Examiner* — Cecilia M Jaisle
(74) *Attorney, Agent, or Firm* — Oblon, Spivak, McClelland, Maier & Neustadt, L.L.P.

(57) ABSTRACT

The present invention is related to pyridine methylene azolidinone derivatives of Formula (I) in particular for the treatment and/or prophylaxis of autoimmune disorders and/or inflammatory diseases, cardiovascular diseases, neurodegenerative diseases, bacterial or viral infections, kidney diseases, platelet aggregation, cancer, transplantation, graft rejection or lung injuries.

15 Claims, No Drawings

OTHER PUBLICATIONS

Muriel Laffargue, et al., "Phosphoinositide 3-Kinase γ is an Essential Amplifier of Mast Cell Function", Immunity, vol. 16, No. 3, pp. 441-451, 2001.

Margaret A. Lawlor, et al.,"PKB/AKT: A Key Mediator of Cell Proliferation, Survival and Insulin Response", Journal of Cell Science, vol. 114, No. 16, pp. 2903-2010, 2001.

Nick R. Leslie, et al., "Phosphoinositide-Regulated Kinases and Phosphoinositide Phosphatases", Chem. Rev. vol. 101, No. 8, pp. 2365-2380, 2001.

Marco Lopez-Ilasaca, et al., "Phosphoinositide 3-Kinase γ is a Mediator of Gβγ-Dependent Jun Kinase Activation", The Journal of Biological Chemistry, vol. 273, No. 5, pp. 2505-2508, 1998.

Francoise Pages, et al., "Binding of Phosphatidylinositol-3-OH Kinase to CD28 is Required for T-Cell Signalling", Nature, vol. 369, pp. 327-329, 1994.

Peter J. Parker, "Pi 3-Kinas Puts GTP on the Rac", Current Biology, vol. 5, No. 6, pp. 577-579, 1995.

Ananthachari Srinivasan, et al., "Pyridopyrimidines. 10. Nucleophilic Substitutions in the Pyrido [3, 2-d] Pyrimidine Series", J. Org. Chem. vol. 44, No. 3, pp. 435-440, 1979.

Robert C. Stein, et al "PI3- Kinase Inhibition: A Target for Drug Development?", Molecular Medicine Today, vol. 6, No. 9, pp. 347-357, 2000.

Lens Stephens, et al., "Roles of PI3KS in Leukocyte Chemotaxis and Phagocytosis", Current Opinion Cell Biology, vol. 14, No. 2, pp. 203-213, 2002.

Marcus Thelen, et al., "Wortmannin Binds Specifically to 1-Phosphatidylinositol 3-Kinase While Inhibiting Guanine Nucleotide-Binding Protein-Coupled Receptor Signaling in Neutrophil Leukocytes", Proc. Natl. Acad. Sci. USA, vol. 91, pp. 2960-4964, 1994.

Lutz F. Tietze, et al., "The Knoevenagel Reaction", Pergamon Press, Oxford, EDS.: Trost B. M., Fleming I, pp. 341-394, 1991.

A Toker, "Phosphoinositides and Signal Transduction", CMLS Cellular and Molecular Life Sciences, vol. 59, No. 5, pp. 761-779, 2002.

Bart Vanhaesebroeck, et al., "Synthesis and Function of 3-Phosphorylated Inositol Lipids", Annu. Rev. Biochem., vol. 70, pp. 535-602, 2001.

Matthias P. Wymann, et al., "Lipids on the Move: Phosphoinositide 3-Kinases in Leukocyte Function", Trends Immunology Today, vol. 21, No. 6, pp. 260-264, 2000.

Ryoji Yao, et al., "Requirement for Phosphatidylinositol-3 Kinase in the Prevention of Apoptosis by Nerve Growth Factor", Science, vol. 267, pp. 2003-2006, 1995.

R. N. P. Singh, et al., "Modified Forms of Human Growth Hormone with with Increased Biological Activities", American Cancer Society, vol. 94, No. 3, pp. 883-891, 1974.

Joseph B. Schwartz, "Pharmaceutical Manufacturing", Part 5 of Remington's Pharmaceutical Sciences, $20^{th}$ Edition Marck Publishing Company, pp. 670-1050, 2000.

Matthew J. Thomas, et al.; "Airway inflammation: chemokine-induced neutrophilia and the class I phosphoinositide 3-kinases"; European Journal of Immunology; 2005; 35; pp. 1283-1291.

Montserrat Camps, et al.; "Blockade of PI3Kγ suppresses joint inflammation and damage in mouse models of rheumatoid arthritis"; Nature Medicine; Sep. 2005; vol. 11;No. 9; pp. 936-943.

Domingo F. Barber, et al.; "PI3Kγinhibition blocks glomerulonephritis and extends lifespan in a mouse model of systemic lupus"; Brief Communications; Nature Medicine; Sep. 2005; vol. 11; No. 9; pp. 933-935.

Carmine Vecchione, et al.; Protection from angiotensin II-mediated vasculotoxic and hypertensive response in mice lacking PI3Kγ; The Journal of Experimental Medicine; Apr. 18, 2005; vol. 201; No. 8; pp. 1217-1228.

Enrico Lupia, et al.; "Ablation of Phosphoinositide 3-kinase-γReduces the Severity of Acute Pancreatitis"; American Journal of Pathology; 2004; 165 (Abstract Only).

M. P. Wymann, et al.; "Phosphoinositide 3-kinaseγ: a key modulator in inflammation and allergy"; Biochemical Society; 2003; pp. 275-280.

Emilio Hirsch, et al.: "Resistance to thromboembolism in PI3Kγ-deficient mice [1]"; The FASEB Journal; Sep. 2001; vol. 15; pp. 2019-2021.

Ho-Kee Yum, et al.;"Involvement of Phosphoinositide 3-Kinases in Neutrophil Activation and the Development of Acute Lung Injury"; The American Association of Immunologists; 2001; pp. 6601-6608.

Enrico Patrucco, et al.; "PI3Kγ Modulates the Cardiac Response to Chronic Pressure Overload by Distinct Kinase-Dependent and-Independent Effects"; Cell Press; Aug. 6, 2004; vol. 118; pp. 375-387.

Annalisa Del Prete, et al.; "Defective dendritic cell migration and activation of adaptive immunity in PI3Kγ-deficient mice"; The EMBO Journal; 2004 European Molecular Biology Organization; vol. 23; No. 17; pp. 3505-3515.

Thomas Rückle, et al.; PI3Kγinhibition: towards an 'aspirin of the 21st century'?; Nature Reviews/Drug Discovery; Nov. 2006; vol. 5; pp. 903-918.

Wikipedia, Phosphoinositide 3-kinase, http://en.wikipedia.or/wiki/Phosphoinositide_3-kinase, downloaded Dec. 31, 2009.

\* cited by examiner

PYRIDINE METHYLENE AZOLIDINONES AND USE THEREOF PHOSPHOINOSITIDE INHIBITORS

CROSS-REFERENCE TO RELATED APPLICATIONS

This application is a divisional of U.S. Ser. No. 11/574,613, filed on Aug. 23, 2007, now U.S. Pat. No. 7,842,698, issued Nov. 30, 2010, which claims benefit of U.S. Prov. No. 60/607,374, filed on Sep. 3, 2004, now expired.

FIELD OF THE INVENTION

This present invention is related to the use of pyridine methylene azolidinone derivatives of Formula (I) for the treatment and/or prophylaxis of autoimmune disorders and/or inflammatory diseases, cardiovascular diseases, neurodegenerative diseases, bacterial or viral infections, allergy, asthma, pancreatitis, multi-organe failure, kidney diseases, platelet aggregation, cancer, sperm motility, graft rejection or lung injuries. Specifically, the present invention is related to pyridine methylene azolidinone derivatives for the modulation, notably the inhibition of the activity or function of the phosphoinositide-3-kinases, PI3Ks.

BACKGROUND OF THE INVENTION

Phosphoinositide 3-kinases (PI3Ks) have a critical signalling role in cell proliferation, cell survival, vascularization, membrane trafficking, glucose transport, neurite outgrowth, membrane ruffling, superoxide production, actin reorganization and chemotaxis (Cantley, 2000, *Science*, 296, 1655-1657 and Vanhaesebroeck et al., 2001, *Annu. Rev. Biochem.*, 70, 535-602).

The term PI3K is given to a family of lipid kinases which, in mammals, consists in eight identified PI3Ks that are divided into three sub-families according to their structure and their substrate specificity.

Class I group of PI3Ks consists in two sub-groups, Class IA and Class IB.

Class IA consists in a 85 kDa regulatory unit (responsible for protein-protein interactions via the interaction of Src homology 2 (SH2) domain with phosphotyrosine residues of other proteins) and a catalytic sub-unit of 110 kDa. Three catalytic forms (p100α, p110β and p110δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic sub-unit complexed with a 101-kDa regulatory protein, p101).

Class II PI3Ks comprises α, β and γ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the haematopoetic cell system, smooth muscle cells, myocytes and endothelial cells (Vanhaesebroeck et al., 1997, *Trends Biochem Sci.*, 22(7), 267-72). Their expression might also be regulated in an inducible manner depending on the cellular-, tissue type and stimuli as well as disease context.

PI3Ks are enzymes involved in phospholipid signalling and are activated in response to a variety of extra-cellular signals such as growth factors, mitogens, integrins (cell-cell interactions) hormones, cytokines, viruses and neurotransmitters and also by intra-cellular cross regulation by other signalling molecules (cross-talk, where the original signal can activate some parallel pathways that in a second step transmit signals to PI3Ks by intra-cellular signalling events), such as small GTPases, kinases or phosphatases for example.

Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)P$_2$), respectively generating three lipid products, namely phosphatidylinositol 3-monophosphate (PI(3)P), phosphatidylinositol 3,4-bisphosphate (PI(3,4)P$_2$) and phosphatidylinositol 3,4,5-trisphosphate (PI(3,4,5)P$_3$ (see Scheme A below).

Scheme A

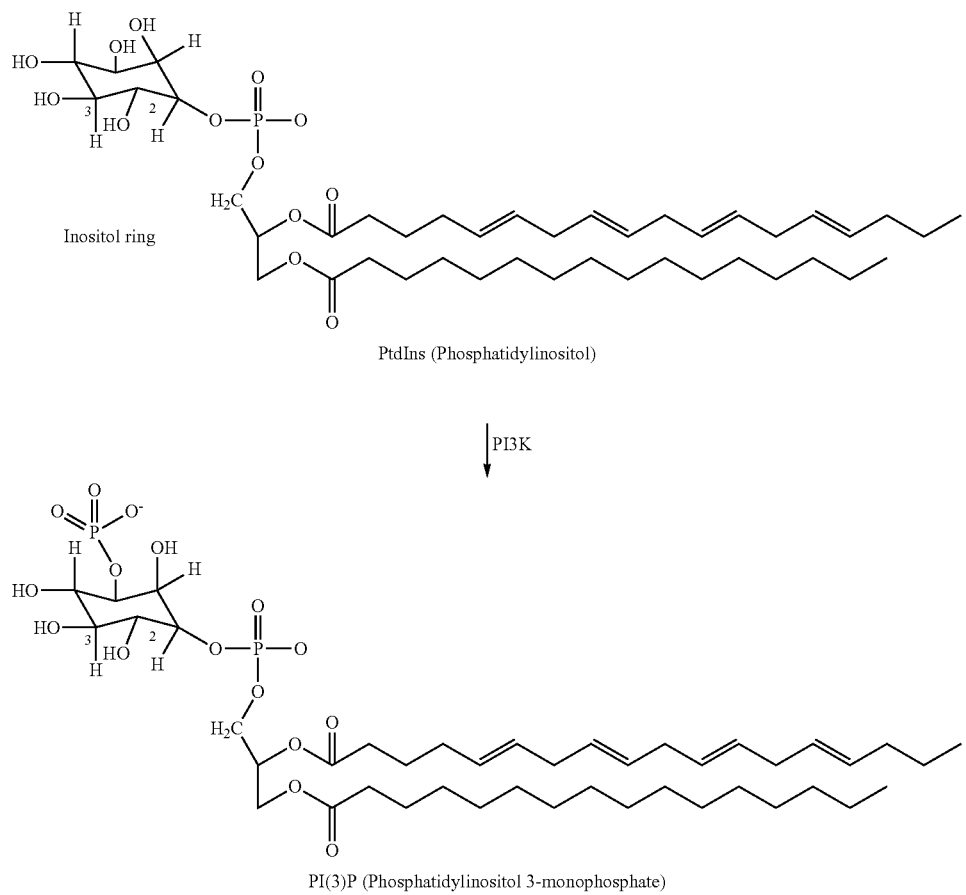

The preferred substrate for Class I PI3Ks is PI(4,5)P$_2$. Class II PIKs have a strong prefererence for PtdIns as substrate over PI(4)P and PI(4,5)P$_2$. Class III PI3Ks can only use PtdIns as substrate in vivo and are likely to be responsible for the generation of most PI(3)P in cells (Vanhaesebroeck et al., 2001, above).

The phosphoinositides intracellular signalling pathway begins with the binding of a signalling molecule (extracellular ligands, stimuli, receptor dimerization, transactivation by heterologous receptor (e.g. receptor tyrosine kinase)) to a G-protein linked transmembrane receptor integrated into the plasma membrane resulting in the activation of PI3Ks.

Once activated, PI3Ks convert the membrane phospholipid PI(4,5)P$_2$ into PI(3,4,5)P$_3$ which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Leslie et al., 2001, *Chem. Rev.* 101(8) 2365-80; Katso et al., 2001, *Annu. Rev. Cell Dev. Biol.* 1, 615-75 and Toker et al., 2002, *Cell Mol. Life Sci.* 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, *Mol. Med. Today* 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, *Immunol Today* 21(6) 260-4; Hirsch et al., 2000, *Science* 287(5455) 1049-53; Hirsch et al., 2001, *FASEB J.* 15(11) 2019-21 and Gerard et al., 2001, *Nat Immunol.* 2(2) 108-15).

PI3-kinase activation, is therefore believed to be involved in a range of cellular responses including cell growth, differentiation and apoptosis (Parker et al., 1995, *Current Biology*, 5, 577-99; Yao et al., 1995, *Science*, 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen (Pages et al., 1994, *Nature*, 369, 327-29). These effects are linked to increases in the transcription of a number of genes including interleukin-2 (IL-2), an important T cell growth factor (Fraser et al., 1991, *Science*, 251, 313-16). Mutation of CD28 such that it can longer interact with PI3-kinase leads to a failure to initiate IL-2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3Kγ has been identified as a mediator of G beta-gamma-dependent regulation of JNK activity wherein G beta-gamma are subunits of heterotrimeric G proteins (Lopez-Ilasaca et al., 1998, *J. Biol. Chem.* 273(5) 2505-8).

Recently, it has been described that PI3Kγ relays inflammatory signals through various G(i)-coupled receptors (Laffargue et al., 2002, *Immunity* 16(3) 441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, *J. Cell. Sci.*, 114 (Pt 16) 2903-1 and Stephens et al., 2002, *Curr. Opinion Cell Biol.* 14(2), 203-13).

Specific inhibitors against individual members of a family of enzymes provide valuable tools for deciphering functions of each enzyme.

Two compounds, LY294002 and wortmannin (cf. hereinafter), have been widely used as PI3-kinase inhibitors. These compounds are non-specific PI3K inhibitors, as they do not distinguish among the four members of Class I PI3-kinases.

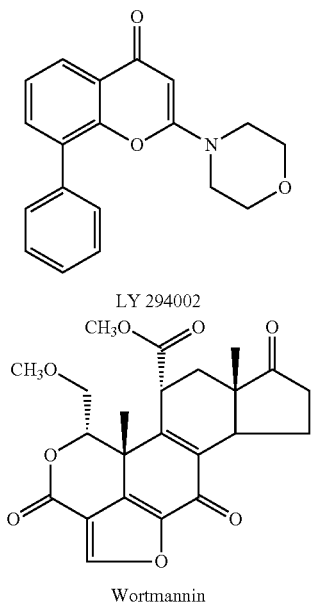

$IC_{50}$ values of wortmannin against each of the various Class I PI3-kinases are in the range of 1-10 nM and $IC_{50}$ values for LY294002 against each of these PI3-kinases are about 15-20 μM (Fruman et al., 1998, *Ann. Rev. Biochem.*, 67, 481-507), also 5-10 mM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al., 1994, *Proc. Natl. Acad. Sci. USA*, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using wortmannin, there is evidence that PI3-kinase function is also required for some aspects of leukocyte signaling through G-protein coupled receptors (Thelen et al., 1994). Morever, it has been shown that wortmannin and LY294002 block neutrophil migration and superoxide release. However, in as much as these compounds do not distinguish among the various isoforms of PI3K, it remains unclear which particular PI3K isoform or isoforms are involved in these phenomena.

Some results have indicated that PI3K inhibitors, for example, LY294002, can increase the in vivo antitumor activity of certain cytotoxic agents (e.g. paclitaxel) (Grant, 2003, *IDrugs*, 6(10), 946-948).

Recently, thiazolidine derivatives have been recently developed as PI3K inhibitors (WO 2004/007491; WO 2004/056820; WO 2004/052373).

WO 2004/007491 discloses azolidinedione-vinyl fused-benzene derivatives of the following structure:

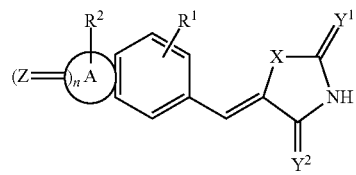

WO 2004/056820 discloses benzoxazine derivatives of the following structure:

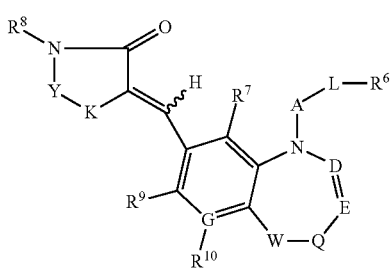

WO 2004/052373 discloses benzoxazin-3-ones derivatives of the following structure:

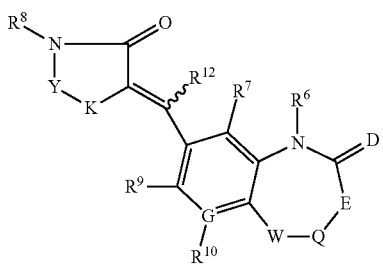

The high relevance of the PI3K pathway in some widespread diseases stresses the need to develop inhibitors, including selective inhibitors, of PIKs.

SUMMARY OF THE INVENTION

It is an object of the invention to provide substances which are suitable for the treatment and/or prevention of disorders related to phosphoinositide-3-kinases, PI3Ks.

It is also an object of the present invention to provide substances which are suitable for the treatment and/or prevention of auto-immune and/or inflammatory disorders.

It is also an object of the present invention to provide substances which are suitable for the treatment and/or prevention of cardiovascular diseases.

It is also an object of the present invention to provide substances which are suitable for the treatment and/or prevention of neurodegenerative disorders.

It is also an object of the present invention to provide substances which are suitable for the treatment and/or prevention of a disorder selected from bacterial and viral infections, kidney diseases, platelet aggregation, cancer, transplantation, graft rejection, lung injuries, respiratory diseases and ischemic conditions.

It is notably an object of the present invention to provide chemical compounds which are able to modulate, especially inhibit the activity or function of phosphoinositide-3-kinases, PI3Ks in disease states in mammals, especially in humans.

It is furthermore an object of the present invention to provide a new category of pharmaceutical formulations for the treatment of and/or diseases mediated selected from auto-immune, inflammatory disorders, cardiovascular diseases, neurodegenerative disorders, bacterial and viral infections, kidney diseases, platelet aggregation, cancer, transplantation, graft rejection, lung injuries, respiratory diseases and ischemic conditions.

It is furthermore an object of the present invention to provide a method for the treatment and/or prevention of disorders selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions.

In a first aspect, the invention provides pyridine methylene azolidinone derivatives of Formula (I):

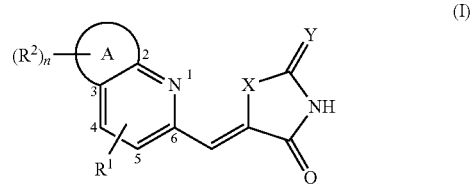

(I)

wherein A, $R^1$, $R^2$, X, Y and n are defined in the detailed description below.

In a second aspect, the invention provides a compound according to Formula (I) for use as a medicament.

In a third aspect, the invention provides a use of a compound according to Formula (I) for the preparation of a pharmaceutical composition for the treatment of a disorder selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions and other diseases and disorders associated with the phosphoinositide-3-kinases, PI3Ks, comprising PI3K α and γ.

In a fourth aspect, the invention provides a pharmaceutical composition comprising at least one a compound according to Formula (I) and a pharmaceutically acceptable carrier, diluent or excipient thereof.

In a fifth aspect, the invention provides a method for treating a patient suffering from a disorder selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions and other diseases and disorders associated with the phosphoinositide-3-kinases, PI3Ks. The method comprises administering a compound according to Formula (I).

In a sixth aspect, the invention provides a method of synthesis of a compound according to Formula (I).

In a seventh aspect, the invention provides compounds according to Formula (II).

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, $C_1$-$C_{12}$-alkyl refers to monovalent alkyl groups having 1 to 12 carbon atoms, including methyl, ethyl, n-propyl, isopropyl, n-butyl, isobutyl, tert-butyl, n-hexyl, heptyl, octyl, nonyl, decly, undecyl, dodecyl and the like "Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, 1-methylpiperazine, morpholine, tetrahydrofurane and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, morpholinylmethyl, morpholinylethyl, morpholinylpropyl, piperidinylethyl, tetrahydrofuranylmethyl and the like.

"Carboxy" refers to the group —C(O)OH.

"$C_1$-$C_6$-alkyl carboxy" refers to $C_1$-$C_6$-alkyl groups having an carboxy substituent, including 2-carboxyethyl and the like.

"Acyl" refers to the group —C(O)R where R includes "$C_1$-$C_6$-alkyl", "aryl", "heteroaryl", "$C_3$-$C_8$-cycloalkyl", "Heterocycloalkyl", "$C_1$-$C_6$-alkyl aryl" or "$C_1$-$C_6$-alkyl heteroaryl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 memebered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", heterocycloalkyl"heterocycloalkyl", "aryl", "heteroaryl","$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including amino-propionic acid ethyl ester and the like.

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"$C_1$-$C_6$-alkyl alkoxy" refers to $C_1$-$C_6$-alkyl groups having an alkoxy substituent, including methoxy, methoxyethyl and the like.

"Alkoxycarbonyl" refers to the group —C(O)OR where R includes H, "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_6$-alkyl alkoxycarbonyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl","$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl","$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl","$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_5$-alkyl groups having an amino substituent, including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "C$_1$-C$_6$-alkyl", "C$_1$-C$_6$-alkyl" substituted with halogens, e.g., an —OSO$_2$—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonyloxy" refers to C$_1$-C$_5$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "C$_1$-C$_6$-alkyl", "C$_1$-C$_6$-alkyl" substituted with halogens, e.g., an —SO$_2$—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonyl" refers to C$_1$-C$_5$-alkyl groups having a sulfonyl substituent, including 2-(methylsulfonyl)ethyl and the like.

"Sulfinyl" refers to a group "—S(O)—R" wherein R is selected from H, "C$_1$-C$_6$-alkyl", "C$_1$-C$_6$-alkyl" substituted with halogens, e.g., a —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfinyl" refers to C$_1$-C$_5$-alkyl groups having a sulfinyl substituent, including 2-(methylsulfinyl)ethyl and the like.

"Sulfanyl" refers to groups —S—R where R includes H, "C$_1$-C$_6$-alkyl", "C$_1$-C$_6$-alkyl" substituted with halogens, e.g., a —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl". Preferred sulfanyl groups include methylsulfanyl, ethylsulfanyl, and the like.

"C$_1$-C$_6$-alkyl sulfanyl" refers to C$_1$-C$_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonylamino" refers to C$_1$-C$_5$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl aminosulfonyl" refers to C$_1$-C$_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "C$_1$-C$_6$-alkyl aryl", "C$_1$-C$_6$-alkyl heteroaryl", "C$_1$-C$_6$-alkyl cycloalkyl", "C$_1$-C$_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Substituted" refers to groups substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "C$_1$-C$_6$-alkyl aryl", "C$_1$-C$_6$-alkyl heteroaryl", "C$_1$-C$_6$-alkyl cycloalkyl", "C$_1$-C$_6$-alkyl heterocycloalkyl", "amino", "aminosulfonyl", "ammonium", "acyl amino", "amino carbonyl", "aryl", "heteroaryl", "sulfinyl", "sulfonyl", "alkoxy", "alkoxy carbonyl", "carbamate", "sulfanyl", "halogen", trihalomethyl, cyano, hydroxy, mercapto, nitro, and the like "Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR, R',R"$^+$Z$^-$, wherein R, R', R" is independently hydrogen, alkyl, or benzyl, C$_1$-C$_6$-alkyl, C$_2$-C$_6$-alkenyl, C$_2$-C$_6$-alkynyl, C$_1$-C$_6$-alkyl aryl, C$_1$-C$_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism.

It has now been found that compounds of the present invention are modulators of the Phosphatoinositides 3-kinases (PI3Ks), comprising PI3K α and γ. When the phosphatoinositides 3-kinase (PI3K) enzyme is inhibited by the compounds of the present invention, PI3K is unable to exert its enzymatic, biological and/or pharmacological effects. The compounds of the present invention are therefore useful in the treatment and prevention of autoimmune disorders and/or inflammatory diseases, cardiovascular diseases, neurodegenerative diseases, bacterial or viral infections, kidney diseases, platelet aggregation, cancer, transplantation, graft rejection or lung injuries.

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The compounds according to Formula (I) are suitable for the modulation, notably the inhibition of the activity of phosphatoinositides 3-kinases (PI3K). It is therefore believed that the compounds of the present invention are also particularly useful for the treatment and/or prevention of disorders, which are mediated by PI3Ks, particularly PI3K α and/or PI3K γ. Said treatment involves the modulation—notably the inhibition or the down regulation—of the phosphatoinositides 3-kinases.

The compounds according to Formula (I) are suitable for use as a medicament.

In one embodiment, the invention provides pyridine methylene azolidinone derivatives of Formula (I):

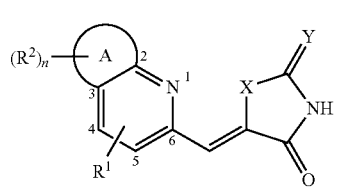

wherein $R^1$ is selected from H, halogen, optionally substituted $C_1$-$C_6$-alkyl, optionally substituted $C_2$-$C_6$-alkenyl, optionally substituted $C_2$-$C_6$-alkynyl, optionally substituted $C_1$-$C_6$-alkyl alkoxy, optionally substituted alkoxycarbonyl, optionally substituted acyl, optionally substituted sulfonyl, optionally substituted sulfanyl, optionally substituted sulfinyl, optionally substituted alkoxy and optionally substituted amino;

$R^2$ is selected from H; halogen; optionally substituted $C_1$-$C_6$-alkyl; optionally substituted to $C_2$-$C_6$-alkenyl; $C_2$-$C_6$-alkynyl; optionally substituted aryl, such as phenyl and 3,5-dimethoxy phenyl; optionally substituted heteroaryl, such as optionally substituted 2,3 di-hydroindolyl (e.g. 2,3-dihydro-indole-1-carboxylic acid tert-butyl ester, 2,3-Dihydro-1H-indol-5-yl, Acetyl-2,3-dihydro-1H-indol-5-yl, 1-(4-Dimethy-lamino-butyryl)-2,3-dihydro-1H-indol-5-yl, 1-Methanesulfonyl-2,3-dihydro-1H-indol-5-yl, 1-Chloromethanesulfonyl-2,3-dihydro-1H-indol-5-yl, 1-(3-Morpholin-4-yl-propane-1-sulfonyl)-2,3-dihydro-1H-indol-5-yl); optionally substituted $C_3$-$C_8$-cycloalkyl; optionally substituted $C_3$-$C_8$-heterocycloalkyl, including optionally substituted piperidinyl such as 1-piperidinyl, 4-fluoro-1-piperidinyl, 4-(trifluoromethyl)-1-piperidinyl; optionally substituted aryl $C_1$-$C_6$-alkyl; optionally substituted heteroaryl $C_1$-$C_6$-alkyl; optionally substituted $C_3$-$C_8$-cycloalkyl $C_1$-$C_6$-alkyl and optionally substituted $C_3$-$C_8$-heterocycloalkyl $C_1$-$C_6$-alkyl; optionally substituted $C_1$-$C_6$-alkyl alkoxy; optionally substituted alkoxycarbonyl; optionally substituted acyl; optionally substituted sulfonyl; optionally substituted sulfanyl; optionally substituted sulfinyl; optionally substituted alkoxy and optionally substituted amino.

X is selected from S, NH and O;
Y is selected from O, S and $NR^3$, wherein $R^3$ is selected from H, optionally substituted $C_1$-$C_6$-alkoxy, optionally substituted $C_1$-$C_6$-alkyl, optionally substituted $C_2$-$C_6$-alkenyl, optionally substituted $C_2$-$C_6$-alkynyl, optionally substituted $C_1$-$C_6$-alkyl aryl, cyano and optionally substituted sulfonyl;
A is an optionally substituted heteroaryl group, including optionally substituted pyrimidinyl, optionally substituted pyrazinyl, optionally substituted furyl and optionally substituted imidazolyl;
n is an integer selected from 1 and 2; as well as its geometrical isomers, its optically active forms as enantiomers, diastereomers and its racemate forms, as well as pharmaceutically acceptable salts thereof.

In a specific embodiment, the invention provides pyridine methylene azolidinone derivatives of Formula (I) wherein $R^1$ is H.

In another specific embodiment, the invention provides pyridine methylene azolidinone derivatives of Formula (I) wherein $R^2$ is H.

In another specific embodiment, the invention provides pyridine methylene azolidinone derivatives of Formula (I) wherein $R^2$ is optionally substituted $C_3$-$C_8$-heterocycloalkyl.

In another specific embodiment, the invention provides pyridine methylene azolidinone derivatives of Formula (I) wherein $R^2$ is selected from optionally substituted aryl and optionally substituted heteroaryl.

In another specific embodiment, the invention provides pyridine methylene azolidinone derivatives of Formula (I) wherein $R^3$ is H.

In another specific embodiment, the invention provides pyridine methylene azolidinone derivatives of Formula (I) wherein X is S.

In another specific embodiment, the invention provides pyridine methylene azolidinone derivatives of Formula (I) wherein Y is O.

In another specific embodiment, the invention provides pyridine methylene azolidinone derivatives of Formula (I) wherein Y is S.

In another specific embodiment, the invention provides pyridine methylene azolidinone derivatives of Formula (I) wherein n is 1.

In another specific embodiment, the invention provides pyridine methylene azolidinone derivatives of Formula (I) wherein n is 2.

In a preferred embodiment, the invention provides pyridine methylene azolidinone derivatives of Formula (I) wherein A is such as it forms together with the pyridine ring the following group (Ia):

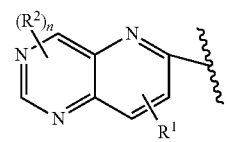

wherein $R^1$, $R^2$ and n are as defined above.

In another preferred embodiment, the invention provides pyridine methylene azolidinone derivatives of Formula (I) wherein A is such as it forms together with the pyridine ring the following group (Ib):

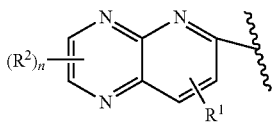

(Ib)

wherein $R^1$, $R^2$ and n are as defined above.

In another preferred embodiment, the invention provides pyridine methylene azolidinone derivatives of Formula (I) wherein A is such as it forms together with the pyridine ring the following group (Ic):

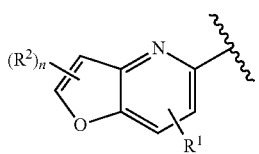

(Ic)

wherein $R^1$, $R^2$ and n are as defined above.

In another preferred embodiment, the invention provides pyridine methylene azolidinone derivatives of Formula (I) wherein A is such as it forms together with the pyridine ring the following group (Id):

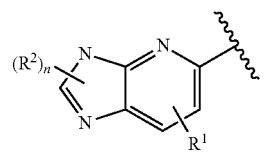

(Id)

wherein $R^1$, $R^2$ and n are as defined above.

In a preferred embodiment, the invention provides pyridine methylene azolidinone derivatives of Formula (I) wherein $R^1$ is H; $R^2$ is optionally substituted $C_3$-$C_8$-heterocycloalkyl; X is S; Y is O or S; A forms together with the pyridine ring a group of Formula (Ia) and n is 1.

In a preferred embodiment, the invention provides pyridine methylene azolidinone derivatives of Formula (I) wherein $R^1$ is H; X is S; Y is O and A forms together with the pyridine ring a group of Formula (Ib).

In a preferred embodiment, the invention provides pyridine methylene azolidinone derivatives of Formula (I) wherein $R^1$ is H; X is S; Y is O and A forms together with the pyridine ring a group of Formula (Ic).

In a preferred embodiment, the invention provides pyridine methylene azolidinone derivatives of Formula (I) wherein $R^1$ is H; X is S; Y is O and A forms together with the pyridine ring a group of Formula (Id).

Compounds of the present invention include in particular those of the group consisting of:

| Example N° | Name |
|---|---|
| 1 | (5Z)-5-{[4-(1-piperidinyl)pyrido[3,2-d]pyrimidin-6-yl]methylene}-1,3-thiazolidine-2,4-dione; |
| 2 | (5Z)-5-{[4-(4-fluoro-1-piperidinyl)pyrido[3,2-d]pyrimidin-6-yl]methylene}-1,3-thiazolidine-2,4-dione; |
| 3 | (5Z)-5-({4-[4-(trifluoromethyl)-1-piperidinyl]pyrido[3,2-d]pyrimidin-6-yl}methylene)-1,3-thiazolidine-2,4-dione; |
| 4 | 5-Pyrido[2,3-b]pyrazin-6-ylmethylene-thiazolidine-2,4-dione; |
| 5 | 5-Furo[3,2-b]pyridine-5-ylmethylene-thiazolidine-2,4-dione; |
| 6 | 5-[4-(4-Fluoro-piperidin-1-yl)-pyrido[3,2-d]pyrimidin-6-ylmethylene]-2-thioxo-thiazolidin-4-one; |
| 7 | 5-(3-Phenyl-3H-imidazo[4,5-b]pyridin-5-ylmethylene)-thiazolidine-2,4-dione; |
| 8 | 5-[3-(3,5-Dimethoxy-phenyl)-3H-imidazo[4,5-b]pyridin-5-ylmethylene]-thiazolidine-2,4-dione; |
| 9 | 5-[5-(2,4-Dioxo-thiazolidin-5-ylidenemethyl)-imidazo[4,5-b]pyridin-3-yl]-2,3-dihydro-indole-1-carboxylic acid tert-butyl ester; |
| 10 | 5-[3-(2,3-Dihydro-1H-indol-5-yl)-3H-imidazo[4,5-b]pyridin-5-ylmethylene]-thiazolidine-2,4-dione; |
| 11 | 5-[3-(1-Acetyl-2,3-dihydro-1H-indol-5-yl)-3H-imidazo[4,5-b]pyridin-5-yl methylene]-thiazolidine-2,4-dione; |
| 12 | 5-{3-[1-(4-Dimethylamino-butyryl)-2,3-dihydro-1H-indol-5-yl]-3H-imidazo[4,5-b]pyridin-5-ylmethylene}-thiazolidine-2,4-dione; |
| 13 | 5-[3-(1-Methanesulfonyl-2,3-dihydro-1H-indol-5-yl)-3H-imidazo[4,5-b]pyridin-5-ylmethylene]-thiazolidine-2,4-dione; |
| 14 | 5-[3-(1-Chloromethanesulfonyl-2,3-dihydro-1H-indol-5-yl)-3H-imidazo[4,5-b]pyridin-5-ylmethylene]-thiazolidine-2,4-dione; |
| 15 | 5-{3-[1-(3-Morpholin-4-yl-propane-1-sulfonyl)-2,3-dihydro-1H-indol-5-yl]-3H-imidazo[4,5-b]pyridin-5-ylmethylene}-thiazolidine-2,4-dione; |
| 16 | 6-[5-(2,4-Dioxo-thiazolidin-5-ylidenemethyl)-imidazo[4,5-b]pyridin-3-yl]-2,3-dihydro-indole-1-carboxylic acid tert-butyl ester; |
| 17 | 5-[3-(1-Methanesulfonyl-2,3-dihydro-1H-indol-6-yl)-3H-imidazo[4,5-b]pyridin-5-ylmethylene]-thiazolidine-2,4-dione. |

The compounds of the present invention are useful as medicaments. They may be used for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation, graft rejection or lung injuries.

In one embodiment, the compounds of Formula (I) are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another embodiment, the compounds of Formula (I) are useful for the treatment and/or prophylaxis of neurodegenerative diseases including Alzheimer's disease, Huntington's disease, CNS trauma, stroke or ischemic conditions.

In still a further embodiment according to the invention, the compounds of Formula (I) are useful for the treatment and/or prophylaxis of cardiovascular diseases such as atherosclerosis, heart hypertrophy, cardiac myocyte dysfunction, elevated blood pressure or vasoconstriction.

In still another embodiment according to the invention, the compounds of Formula (I) are useful for the treatment and/or prophylaxis of chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastisis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

In another embodiment according to the invention, is provided a process for the preparation of pyridine methylene azolidinone derivative according to Formula (I), comprising the step of reacting a compound of Formula (II) with a derivative of Formula (III) in presence of a base:

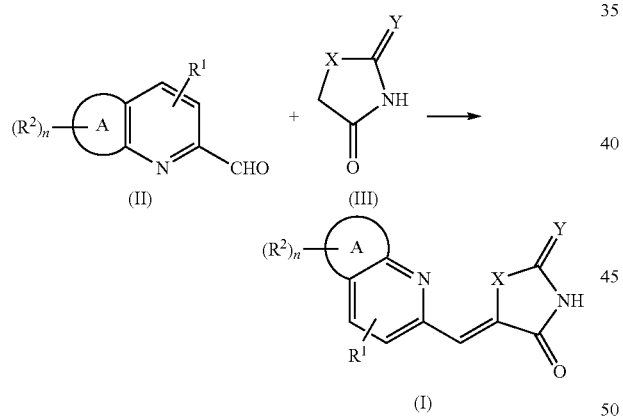

wherein $R^1$, $R^2$, A, X, Y and n are defined above.

In another embodiment according to the invention, are provided compounds according to Formula (II):

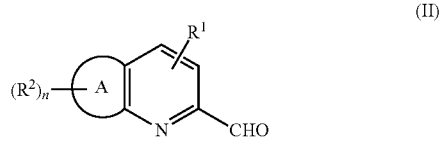

wherein $R^1$, $R^2$, A, X, Y and n are defined above and wherein the compounds of Formula II are selected from the group of formulae (IIa), (IIb) and (IIc):

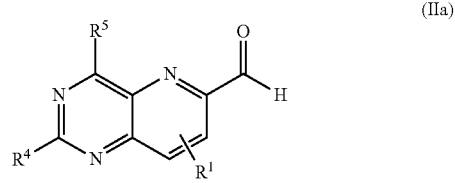

wherein $R^4$ is selected from H and $R^2$; $R^5$ is a $R^2$ group wherein the first atom attached to the pyrimidine ring is selected from C, N, S and O and wherein when $R^4$ is $NH_2$, $R^5$ is not $NH_2$; $R^1$, $R^2$ and n are as defined above;

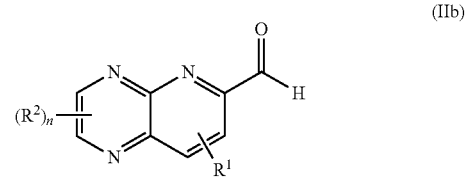

wherein $R^1$, $R^2$ and n are as defined above;

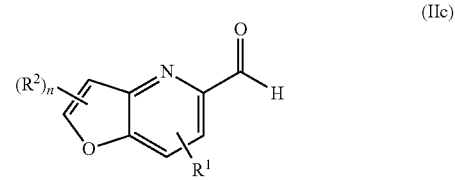

wherein $R^1$, $R^2$ and n are as defined above and wherein at least one $R^1$ or $R^2$ is not H; and

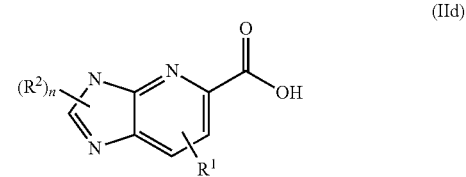

wherein $R^1$, $R^2$ and n are as defined above with the proviso that the compound of Formula (IId) is not 2-(4-methoxyphenyl)-3H-Imidazo[4,5-b]pyridine-5-carboxaldehyde (RN 142764-79-2).

In a further embodiment according to the invention, are provided compounds according to Formula (II) from the group:
4-Piperidin-1-yl-pyrido[3,2-d]pyrimidine-6-carbaldehyde;
4-(4-Fluoro-piperidin-1-yl)-pyrido[3,2-d]pyrimidine-6-carbaldehyde;
4-(4-Methyl-piperidin-1-yl)-pyrido[3,2-d]pyrimidine-6-carbaldehyde;
Pyrido[2,3-b]pyrazine-6-carbaldehyde;
2-Trimethylsilanyl-furo[3,2-b]pyridine-5-carbaldehyde;
3-Phenyl-1H-imidazo[4,5-b]pyridine-5-carbaldehyde;
3-(3,5-Dimethoxyphenyl)-3H-imidazo[4,5-b]pyridine-5-carbaldehyde;
Tert-butyl 5-(5-formyl-3H-imidazo[4,5-b]pyridin-3-yl)indoline-1-carboxylate;

3-(1-acetyl-2,3-dihydro-1H-indol-5-yl)-3H-imidazo[4,5-b]pyridine-5-carbaldehyde;
3-{[4-(dimethylamino)butanoyl]-2,3-dihydro-1H-indol-5-yl}-3H-imidazo[4,5-b]pyridine-5-carbaldehyde;
3-[1-(methylsulfonyl)-2,3-dihydro-1H-indol-5-yl]-3H-imidazo[4,5-b]pyridine-5-carbaldehyde;
3-{1-[(chloromethyl)sulfonyl]-2,3-dihydro-1H-indol-5-yl}-3H-imidazo[4,5-b]pyridine-5-carbaldehyde;
3-{1-[(3-morpholin-4-ylpropyl)sulfonyl]-2,3-dihydro-1H-indol-5-yl}-3H-imidazo[4,5-b]pyridine-5-carbaldehyde;
Tert-butyl 6-(5-formyl-3H-imidazo[4,5-b]pyridin-3-yl)indoline-1-carboxylate;
3-[1-(methylsulfonyl)-2,3-dihydro-1H-indol-6-yl]-3H-imidazo[4,5-b]pyridine-5-carbaldehyde.

The pyridine methylene azolidinone derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing pyridine methylene azolidinone derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyridine methylene azolidinone derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the pyridine methylene azolidinone derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel pyridine methylene azolidinone derivatives according to Formula (I) can be prepared from readily available starting materials by several synthetic approaches, using both solution-phase and solid-phase chemistry protocols (Brummond et al., 1999, *J.O.C.*, 64, 1723-1726). Examples of synthetic pathways for the will be described.

The following abbreviations refer respectively to the definitions below:

Å (Angström), cm (centimeter), eq (equivalent), h (hour), g (gram), M (molar), MHz (Megahertz), µl (microliter), min (minute), mg (milligram), mL (milliliter), mm (millimeter), mmol (millimole), mM (millimolar), nm (nanometer), rt (room temperature), ACN (acetonitrile), ATP (Adenoside Triphosphate), BSA (Bovine Serum Albumin), DCM (dichloromethane), DIBAL (Diisobutylaluminiumhydride), DMF (dimethyl formamide), DMSO (Dimethyl Sulfoxide), HPLC (High Performance Liquid Chromatography), Ins1P (D-myo-inositol-1-phosphate), IR (Infrared), LC (Liquid chromatography), MS (mass spectrometry), NMR (Nuclear Magnetic Resonance), PBS (Phosphate Buffered Saline), PIs (Phosphoinositides), PI3Ks (Phosphoinositide 3-kinases), PI(3)P (Phosphatidylinositol 3-monophosphate), PI(3,4)P$_2$ (Phosphatidylinositol 3,4-bisphosphate), PI(3,4,5)P$_3$ (Phosphatidylinositol 3,4,5-trisphosphate), PI(4)P (Phosphatidylinositol-4-phosphate), PI(4,5)P$_2$) (Phosphatidyl inositol-4,5-biphosphate), PtdIns (Phosphatidylinositol), PVT (polyvinyl toluene), SPA (Scintillation Proximity Assay), TEA (triethylamine), TFA (trifluoro-acetic acid), THF (tetrahydrofuran), TLC (Thin Layer Chromatography), TMS (Trimethylsilyl), UV (Ultraviolet).

The pyridine methylene azolidinone derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In the process illustrated in the following schemes $R^1$, $R^2$, A, X, Y and n are each as above-defined in the description.

Generally, the pyridine methylene azolidinone derivatives according to the general Formula (I) could be obtained by several synthetic approaches, using both solution-phase and solid-phase chemistry protocols (Brummond et al., 1999, above), either by conventional methods or by microwave-assisted techniques.

In a first step, an aldehyde reactant P1 (P1a, P1b, P1c, P1d) and one to two equivalents of reactant P2 (in particular thiazolidinedione or rhodanine) are heated in the presence of a preferably mild base to provide the corresponding olefin of Formula (I) as shown on Scheme 1 below. In the first step, P1 may be replaced by precursors P1a, P1b, P1c and P1d in order to obtain the final compounds (Ia), (Ib) (Ic) and (Id) respectively as above described in the description.

Scheme 1:

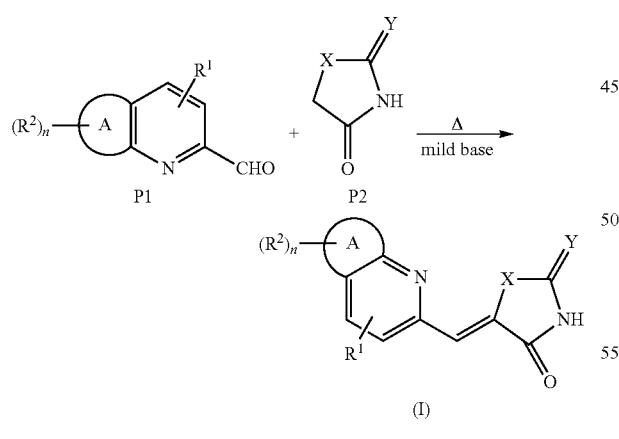

Particularly preferred processes according to the invention are illustrated by the following Schemes 2, 3, 4 and 5 in which compounds of formula (Ia), (Ib), (Ic) and (Id) respectively, may be obtained using the same reaction conditions as above-mentioned.

Scheme 2:

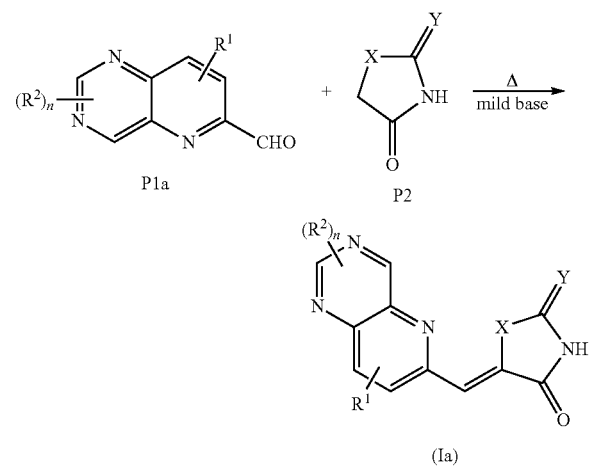

Scheme 3:

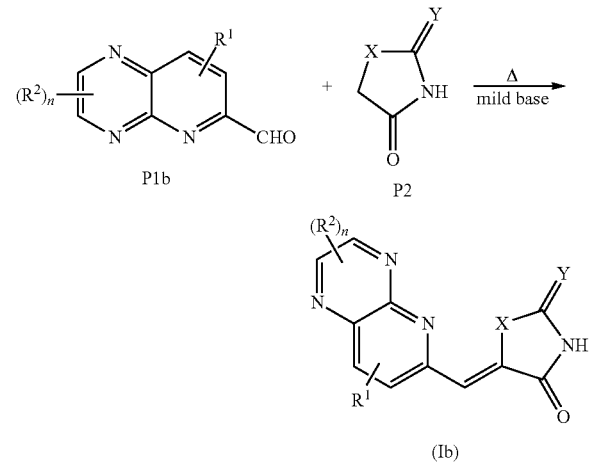

Scheme 4:

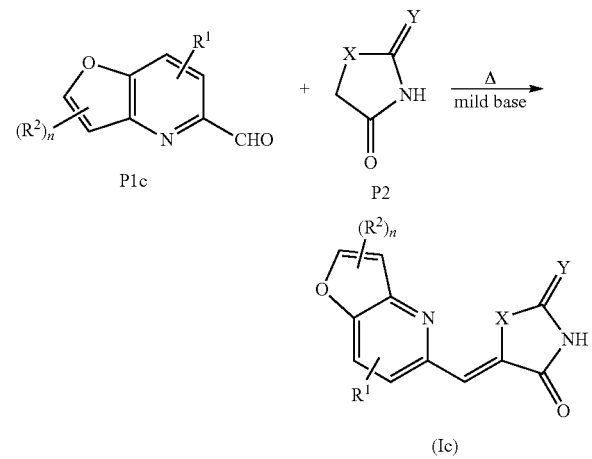

Scheme 5:

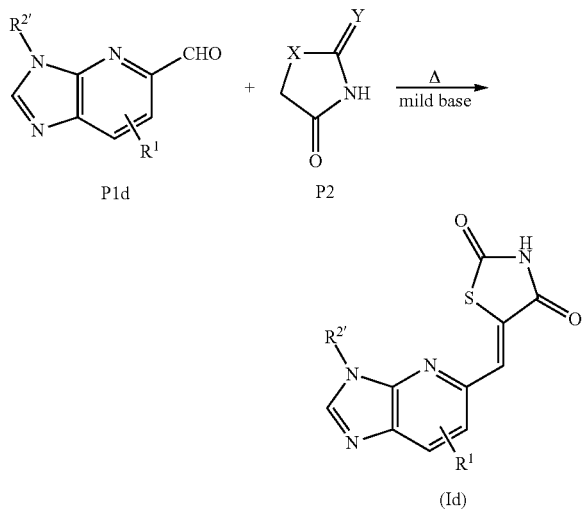

While this step may be carried out in the absence of a solvent at a temperature, which is sufficiently high to cause at least partial melting of the reaction mixture, it is preferably carried out in the presence of an inert solvent. A preferred temperature range is from about 70° C. to 250° C., and especially preferred is a temperature of from about 80° C. to 120° C. Examples of such solvents for the above reaction include solvents like dimethoxymethane, xylene, toluene, o-dichlorobenzene and methanol. Examples of suitable mild bases for the above reaction are alkali metal and alkaline earth salts of week acids such as the ($C_1$-$C_{12}$)-alkyl carboxylic acids and benzoic acid, alkali metal and alkaline earth carbonates and bicarbonates such as calcium carbonate, magnesium carbonate, potassium bicarbonate and secondary amines such as piperidine, morpholine or pyrrolidine as well as tertiary amines such as pyridine, triethylamine, diisopropylethylamine, N-methylmorpholine, N-ethylpiperidine, N-methylpiperidine and the like. Especially preferred mild bases are sodium acetate or pyrrolidine for reasons of economy and efficiency.

In such a typical reaction (Tietze et al., in "*The Knoevenagel reaction*", p. 341 ff., Pergamon Press, Oxford 1991, Eds.: Trost B. M., Fleming I.) the aldehyde P1 and the other starting material (e.g. thiazolidinedione) P2 are combined in approximately equimolar amounts with 0.5 to one equivalent of pyrolidine in methanol or similar solvent and heated between 70 and 200° C. at which the reaction is substantially complete in about 15 minutes to 3 hours. The desired olefin of Formula (I) is then isolated by filtration, in case it would have precipitated out of the reaction mixture upon cooling, or for example, by mixing with water and subsequent filtration, to obtain the crude product. The crude product is purified, if desired, e.g. by crystallization or by standard chromatographic methods.

Alternatively compounds of Formula (I) may be obtained typically by mixing equimolar amounts of thiazolidinedione P2 with aldehyde P1 with molar excess of anhydrous sodium acetate and the mixture is heated at a temperature high enough to effect melting, at which temperature the reaction is mainly complete in about 5 to 60 minutes.

Preferably, the above reaction is carried out in acidic media such as acetic acid in the presence of sodium acetate or beta-alanine.

More preferably, the above reaction is carried out in methanol using 1.1 to 2.0 equivalents of thiazolidinedione P2, one equivalent of aldehyde P1 and 0.2 to 0.5 equivalents of pyrrolidine in methanol.

The reactions described above may be carried out alternatively under microwave conditions as heating source. Typically, the aldehyde starting material P1 and thiazolidinedione P2 are combined in approximately equimolar amounts with 0.5 to one equivalent of piperidine in dimethoxymethane or similar solvent and heated between 140° C. and 240° C. at which the reaction is substantially complete in about 3 to 10 minutes.

The pharmaceutically acceptable cationic salts of compounds of the present invention are readily prepared by reacting the acid forms with an appropriate base, usually one equivalent, in a co-solvent. Typical bases are sodium hxdroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

2,4-Azolidinone derivatives P2 are commercially available from various sources.

Methods of Preparing Intermediates of Compounds of Formula (I).

The aldehydes of formula P1 are prepared by a variety of well known methods, for example by oxido-reduction starting from the corresponding carboxylic acid alkyl ester or carboxylic acid.

Standard techniques to reduce carboxylic acid alkyl ester, carboxylic halides or carboxylic acid to benzylic alcohols use lithium aluminium hydride, diisopropylaluminum, lithium aluminium tri-tert-butoxyhydride etc.

Ultimately, the corresponding benzylic alcohol is re-oxidized to the corresponding aldehyde by mild oxidation with reagents such as manganese dioxide, chromic acid, Dess-Martin reagent or Swern oxidation, or under other conditions known to produce aldehydes from primary alcohols. An alternative way may be the direct reduction of the corresponding carboxylic acid alkyl ester or carboxylic acid to the corresponding aldehyde, using DIBAL at low temperature or any other techniques known in the field.

An alternative way to prepare the appropriate aldehyde P1 is the selective reduction of a nitrile moiety to the corresponding aldehyde using known methods like e.g. DIBAL.

Another way to obtain aldehydes of formula P1 is the selective reduction of the corresponding acyl chloride using e.g. lithiumaluminium-tri-tert-butoxyhydride (Cha et al., 1993, *J.O.C*, 58, p. 4732-34).

Another way to synthesize aldehydes P1 is to start from the corresponding 2-pyridine halides, which are submitted to organometallic assisted reaction in order to afford the corresponding 2-vinyl-pyridines, which ultimately can be oxidized to the corresponding aldehydes P1 using standard oxidation agents for olefinic bonds such as osmium tetroxide, ruthenium tetroxide, ozone, ruthenium(III)chloride in the presence of sodium periodate and others known to person skilled in the art.

Another way to obtain the corresponding aldehydes P1 is the oxidation of a 2-methylpyridine using oxidizing agents such as selenium dioxide or benzene seleninic anhydride.

Acccording to a more particularly preferred process of the invention, as illustrated by Scheme 6 below, reactant P1a can be obtained starting from a derivative of formula P3a wherein R is selected from methyl, ethyl or any other group susceptible to reduction known to the person skilled in the art, by optionally applying a reduction/oxidation sequence using preferably lithium aluminium hydride in tetrahydofuran, followed by an oxidation step using preferably manganese dioxide in dichloromethane.

Scheme 6:

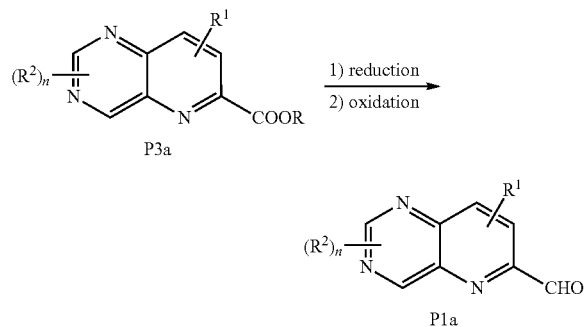

An intermediate that can be used for to above synthesis is methyl 2,4,8-trichloropyrido[3,2-d]pyrimidine-6-carboxylate (Intermediate 1.3), which synthesis is described in the literature (Srinivasan et al., 1979, *J.O.C*, 1979, 44, 3, p. 435), as shown in Scheme 7 below.

Scheme 7:

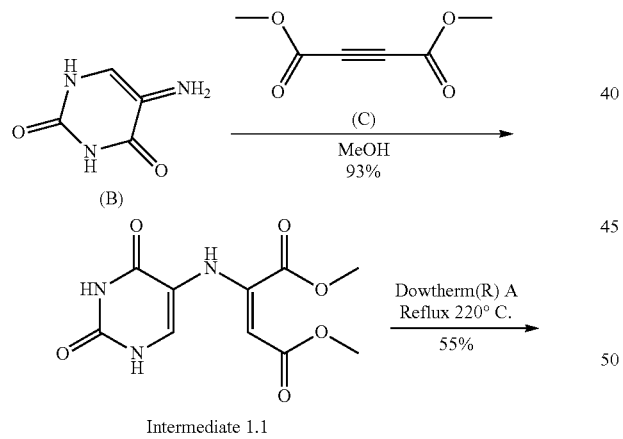

Intermediate 1.1

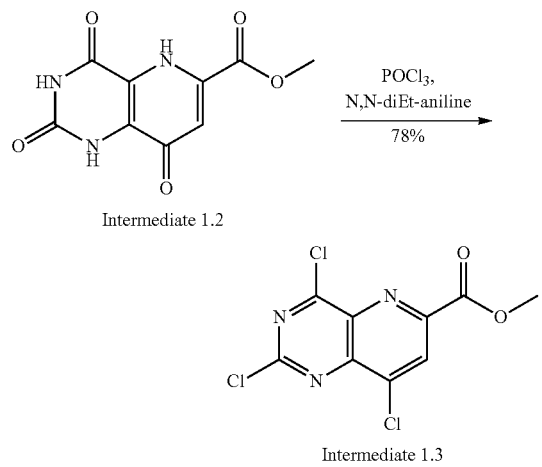

The selective replacement of the 3 chloro groups may allow the introduction of $R^1$ and $R^2$ groups leading to different intermediates of formula P3a (P3a(1), P3a(2), P3a(3), P3(4), P3a(5), P3a(6), P3a(7)) as shown in Scheme 8 below.

Scheme 8:

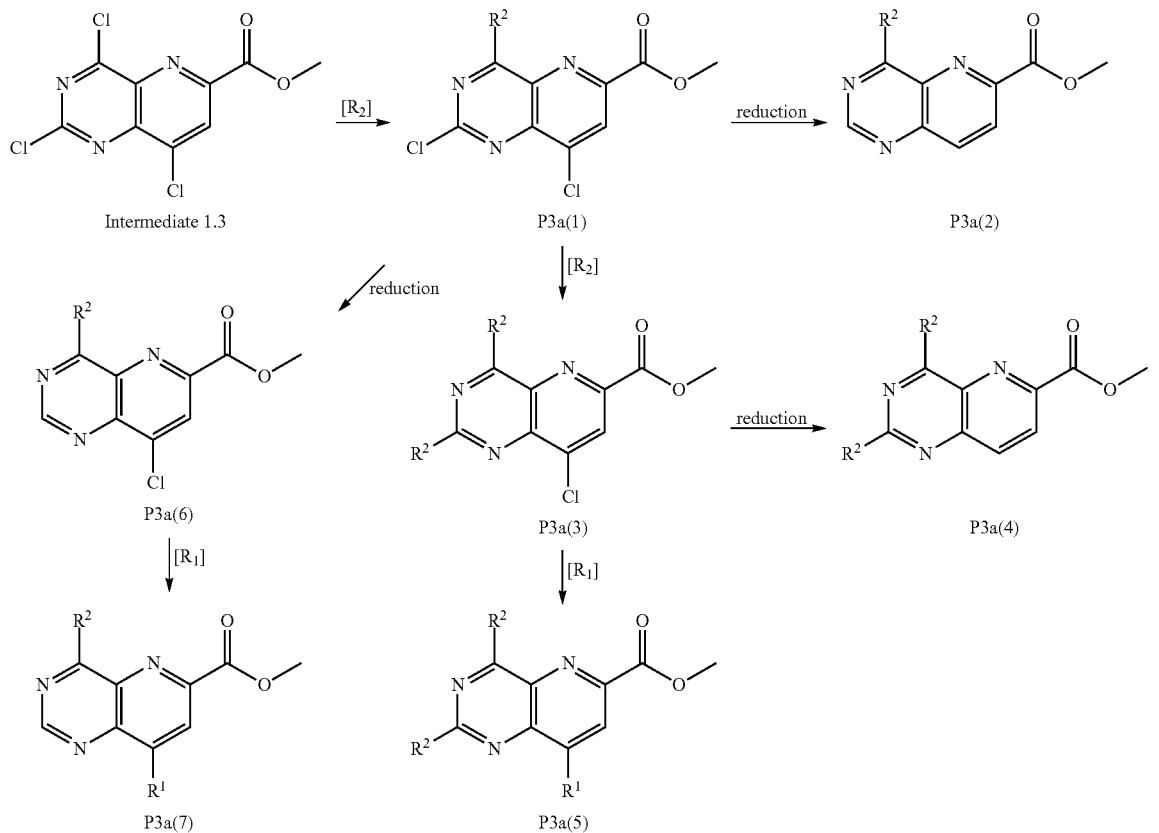

Reductions steps in Scheme 8 can be carried out using standard reducing agents such hydrogen or Raney-Nickel dithiation (Srinivasan et al., 1979, above).

Preferably, the reduction is conducted under mild conditions using ammonium formate in the presence of palladium. The amount of ammonium formate is determined by the numbers of chlorine atoms to be removed (2-12 eq.).

The introduction of groups $R^2$ and $R^1$ is obtained through standard reaction techniques known to the person skilled in the art.

According to another particularly preferred process of the invention, as illustrated by Scheme 9 below, aldehyde P1b can be obtained starting from an intermediate P3b by oxidative cleavage of an olefinic double bond.

Scheme 9:

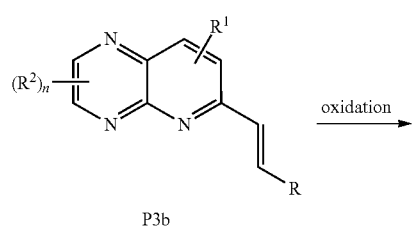

-continued

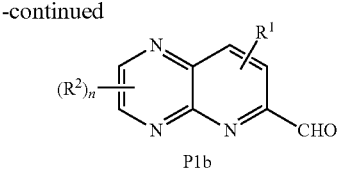

wherein R is selected from H, optionally substituted $C_1$-$C_6$ alkyl, optionally substituted aryl. In such a reaction the olefinic double bond is cleaved using oxidation agents for olefinic bonds such as osmium tetroxide, ruthenium tetroxide, ozone, ruthenium(III)chloride in the presence of sodium periodate and others known to person skilled in the art.

Intermediate P3b can be synthesized starting from 2-halogen pyridine derivatives using organometallic assisted coupling reactions to introduce a vinyl moiety in standard fashion known to the person skilled in the art. The corresponding 2-halogen pyridines are readily accessible from e.g. 2-halogen-4-nitro-6-aminopyridine as depicted in Scheme 10 below, wherein "Hal" represents a halogen.

Scheme 10:

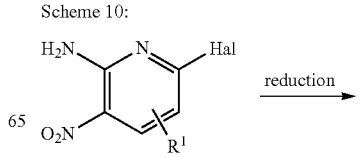

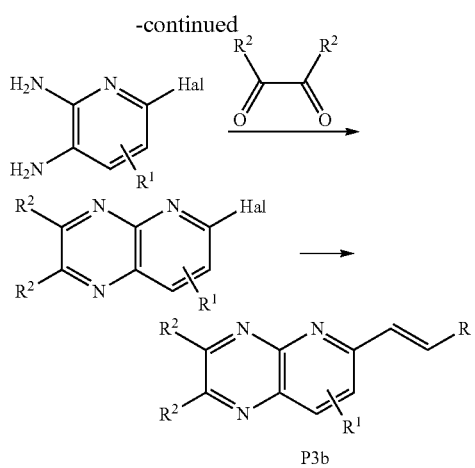

1616) leads to the corresponding acetyl protected alcohol, which in turn can be deprotected and desilylated simultaneously by treatment with sodium hydroxide (2N) in methanol at room temperature. Finally, primary alcohol P3c″ can oxidized to the corresponding aldehyde intermediate P1c using oxidants like manganese dioxide in dichloromethane or any oxidants known to person skilled in the art (Scheme 11 above).

Acccording to another particularly preferred process of the invention, where aza-benzimidazoles are represented, Intermediate P4d can be obtained from intermediate P5d, as depicted in Scheme 12 below, wherein "Hal" represents a halogen.

Scheme 12

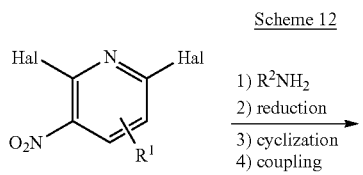

According to another particularly preferred process of invention, as illustrated by Scheme 11 below, wherein R is selected from H, optionally substituted $C_1$-$C_6$ alkyl, optionally substituted aryl, intermediate P1c can be obtained starting from intermediate P3c by oxidation of 2-methyl pyridines.

Scheme 11:

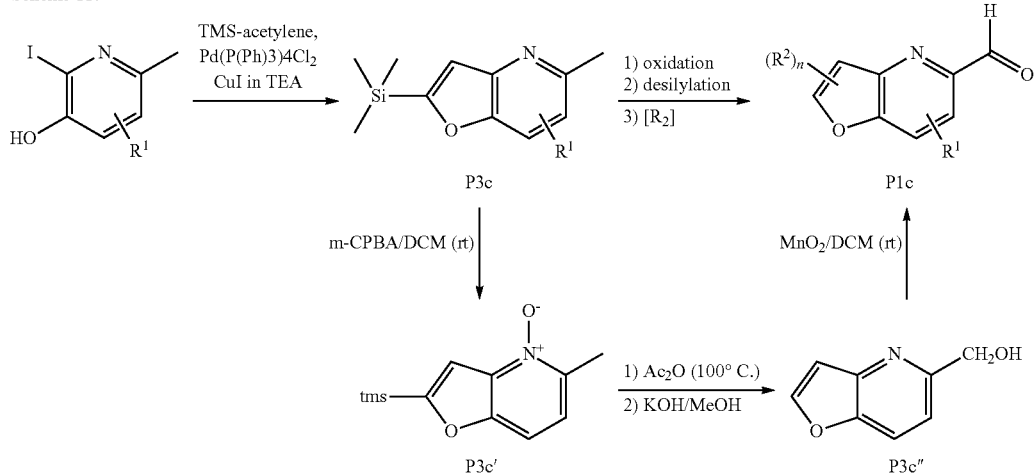

Such oxidation can be carried out using selenium dioxide or benzene seleninic anhydride in an inert solvent at temperatures between 150 to 250° C. Preferably, such a reaction is carried out using microwave as heating source. In a second step, desilylation is performed under standard conditions as described in Kocienski, 1994 (above) and Greene et al., 1999 (above).

Preferably the trimethylsilyl group is cleaved using sodium hydroxide from 2 to 5N.

The introduction of $R^2$ may be performed as described in WO2004/007491.

According to another more preferred process, intermediate P1c can be obtained from intermediate P3c via a picoline N-oxide rearrangement: Typically intermediate P3c is subjected to N-oxidation leading to intermediate P3′, using oxidants like m-Chloro-perbenzoic acid (m-CPBA) at room temperature or any oxidant know to the person skilled in the art. Subsequent basic work-up and heating P3c′ in acetic anhydride at 100° C. for 5 to 15 min (Cava et al., 1958, JOC, 23,

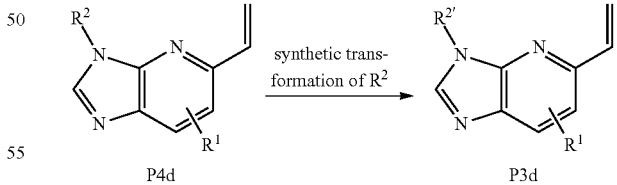

Substitution of the 2-halogen with $R^2NH_2$ in alcohols (e.g. ethanol) in the presence of a base is followed by reduction of the nitro group catalyzed by indium metal in the presence of a hydrogen source. P4d is obtained by subsequent cyclization by means of condensation with amidines followed by installation of a vinyl moiety using organometallic assisted coupling reactions in standard fashion known to the person skilled in the art.

When $R^2$ in intermediate P4d is a chemical moiety which is to undergo synthetic transformations, these transformations are carried out after completion of the coupling with the vinyl moiety. These synthetic transformations include, but are not limited to, deprotections, couplings, oxidations, reductions.

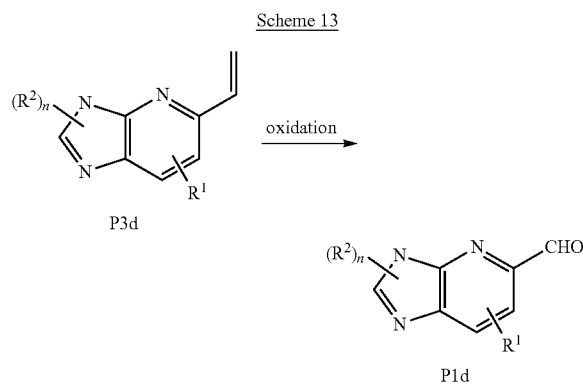

Scheme 13

In accordance with a particularly preferred process of the invention, the installed vinyl olefin bond of intermediate P3d (Scheme 13 above) is cleaved using oxidation agents for olefinic bonds such as osmium tetroxide or ruthenium(III) chloride in the presence of sodium periodate, ozone, and others known to person skilled in the art.

According to a further general process, compounds of Formula (I) can be converted to alternative compounds of Formula (I), employing suitable interconversion techniques well known by a person skilled in the art.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Kocienski, 1994 (above) and Greene et al., 1999 (above).

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

EXAMPLES

The following starting materials commercially available were used:
5-aminouracil commercially available from Aldrich;
Dimethyl acetylenedicarboxylate commercially available from Aldrich;
N,N-diethylaniline commercially available from Aldrich;
Phosphorus oxychloride commercially available from Aldrich;
N-ethyldiisopropylamine commercially available from Aldrich;
Ammonium formate commercially available from Aldrich;
Lithium aluminum hydride commercially available from Aldrich;
Manganese oxide commercially available from Aldrich;
2,4-thiazolidinedione commercially available from Aldrich;
Rhodanine commercially available from Aldrich;
Beta-alanine commercially available from Aldrich;
4-fluoro-piperidine commercially available from Fluorochem;
4-trifluoromethyl-piperidine commercially available from Lancaster;
Glyoxal (Oxaldehyde) commercially available from Aldrich;
Tetrakis(triphenylphosphine)palladium commercially available from Aldrich;
Vinyltributylstannane commercially available from Aldrich;
6-iodo-2-picolin-5-ol commercially available from Acros;
(trimethylsilyl)acetylene commercially available from Aldrich;
Dichlorobis(triphenyl phosphine)palladium(II) commercially available from Aldrich;
1,2 dichloro benzene commercially available from Aldrich;
2-amino-3-nitro-6-chloropyridine commercially available from ACROS;
Indium powder commercially available from Aldrich;
Formamidine acetate commercially available from Aldrich;
Tributyl(vinyl)tin commercially available from Aldrich;
Osmium tetroxide commercially available from Aldrich;
Sodium periodate commercially available from Aldrich;
2,6-Dichloro-3-nitropyridine commercially available from Aldrich;
3,5-Dimethoxyaniline commercially available from Aldrich;
5-Nitroindoline commercially available from Aldrich;
6-Nitroindoline commercially available from Aldrich;
4-(Dimethylamino)butyric acid hydrochloride commercially available from Aldrich;
3-Chloropropanesulfonyl chloride commercially available from Aldrich;
Chloromethanesulfonyl chloride commercially available from Alfa Aesar.

The HPLC, NMR and MS data provided in the examples described below are obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

Preparative HPLC purifications are performed with HPLC Waters Prep LC 4000 System equipped with columns Prep Nova-Pak®HR C186 μm 60 Å, 40×30 mm (up to 100 mg) or with XTerra® Prep MS C8, 10 μm, 50×300 mm (up to 1 g). All the purifications are performed with a gradient of MeCN/H$_2$O 0.09% TFA. The semi-preparative reverse-phase HPLC are performed with the Biotage Parallex Flex System equipped with colums Supelcosil™ ABZ+Plus (25 cm×21.2 mm, 12 μm); UV detection at 254 nm and 220 nm; flow 20 mL/min (up to 50 mg). TLC Analysis is performed on Merck Precoated 60 F$_{254}$ plates. Purifications by flash chromatography are performed on SiO$_2$ support, using cyclohexane/EtOAc or DCM/MeOH mixtures as eluents.

Intermediate 1.1: Dimethyl(2E)-2-[(2,4-dioxo-1,2,3,4-tetrahydro-5-pyrimidinyl)-amino]-2-butenedioate
(Scheme 7)

To a suspension of 5-aminouracil (B)(4.0 g; 31.5 mmol; 1 eq.) in MeOH (120.00 mL) was added dimethyl acetylenedicarboxylate (C) (5.0 g; 35.2 mmol; 1.1 eq.). The suspension was stirred at room temperature for 46 h. The reaction was monitored by NMR. The solid was filtered to afford dimethyl (2E)-2-[(2,4-dioxo-1,2,3,4-tetrahydro-5-pyrimidinyl) amino]-2-butenedioate (8.0 g, 95%) (Intermediate 1.1).

Amount: 8.0 g; Yield: 95%; Formula: $C_{10}H_{11}O_6N_3$; HPLC Purity: 95%; HPLC ($H_2O$ TFA 0.1%-ACN TFA 0.05%): Rt (min); Area %=1.37; 93.61; 1H NMR (DMSO-d6) δ 3.64 (s, 3H), 3.66 (s, 3H), 5.21 (s, 1H), 7.42 (s, 1H), 9.07 (s, 1H), 10.86 (br, 1H), 11.31 (br, 1H); LC-MS: M/Z ESI: Rt (min) 0.85; 210, 238, 270 (M+1); 208, 236, 268 (M−1).

Intermediate 1.2: Methyl 2,4,8-trioxo-1,2,3,4,5,8-hexahydropyrido[3,2-d]pyrimidine-6-carboxylate (Scheme 7)

In a 2 liter-4 neck flask fitted with a reflux condenser was placed dimethyl (2E)-2-[(2,4-dioxo-1,2,3,4-tetrahydro-5-pyrimidinyl)amino]-2-butenedioate (Intermediate 1.1) (38.5 g; 0.14 mol; 1 eq.) dowtherm(R) A (1 L)(phenyl ether-biphenyl eutectic). The suspension was stirred with a mechanical stirrer under argon and heated to 220° C. The reaction was monitored by HPLC/LC/MS. After 3 hours the reaction was stopped by cooling followed by the addition of 300 mL of petroleum ether. The resulting precipitate was filtered and washed with DMF (2×100 mL). Methyl 2,4,8-trioxo-1,2,3,4,5,8 hexahydropyrido[3,2-d]pyrimidine-6-carboxylate (21.02 g; 62%) (Intermediate 1.2) was isolated as a yellow powder in 100% HPLC purity.

Amount: 21.0 g; Yield: 62%; Formula: $C_9H_7O_5N_3$; 1H NMR (DMSO-d6) δ 3.87 (s, 3H), 7.58 (s, 1H), 10.90 (s, 1H), 11.56 (s, 1H), 12.10 (br, 1H).

Intermediate 1.3: Methyl 2,4,8-trichloropyrido[3,2-d]pyrimidine-6-carboxylate (Scheme 7)

A solution of methyl 2,4,8-trioxo-1,2,3,4,5,8-hexahydropyrido[3,2-d]pyrimidine-6-carboxylate (Intermediate 1.2) (9 g; 37.95 mmol; 1 eq.) and N,N-diethylaniline (10 mL) in phosphorus oxychloride (174 mL) was heated at reflux overnight. The solution was concentrated in vacuum. The black oil was poured slowly onto ice. Ethyl acetate was added and the organic phase was washed with water until pH=6. The organic layers were dried over magnesium sulfate, filtered and concentrated. Methyl 2,4,8-trichloropyrido[3,2-d]pyrimidine-6-carboxylate (Intermediate 1.3) (6.5 g, 59%) was precipitated in cyclohexane as a pink solid in 98% HPLC purity. Amount: 6.5 g; Yield: 59%; Formula: $C_9H_4O_2Cl_3N_3$; 1H NMR (CDCl3) δ 4.12 (s, 3H), 8.70 (s, 1H); HPLC ($H_2O$ TFA 0.1%-ACN TFA 0.05%): Rt (min); Area %=3.07; 98; LC-MS: M/Z ESI: Rt (min) 1.58; 293 (M+1).

Intermediate 1.4: Methyl 2,8-dichloro-4-(1-piperidinyl)pyrido[3,2-d]pyrimidine-6-carboxylate (Scheme 8)

To a solution of methyl 2,4,8-trichloropyrido[3,2-d]pyrimidine-6-carboxylate (4.65 g; 15.9 mmol; 1 eq.) (Intermediate 1.3) in acetonitrile (140 mL) was added N-ethyldiisopropyl amine (4 mL; 23.8 mmol; 1.5 eq.). The mixture was cooled down to 0° C. A solution of piperidine (1.57 mL; 15.9 mmol; 1 eq.) in acetonitrile (20 mL) was added dropwise. The mixture was stirred 15 min at 0° C. The mixture was partly concentrated and the precipitate was filtered, washed with MeOH and dried under vacuum to afford methyl 2,8-dichloro-4-(1-piperidinyl)pyrido[3,2-d]pyrimidine-6-carboxylate (Intermediate 1.4) (3.98 g; 73%) as a pink solid in 98.8% HPLC purity; Amount: 3.98 g; Yield: 73%; Formula: $C_{14}H_{14}O_2Cl_2N_4$; 1H NMR (DMSO-d6) δ 1.71 (sl, 6H), 3.92 (s, 3H), 4.01 (sl, 2H), 4.82 (sl, 2H), 8.42 (s, 1H); LC-MS: M/Z ESI: Rt (min) 2.02; 341.02, 342.89 (M+1); HPLC ($H_2O$ TFA 0.1%-ACN TFA 0.05%): Rt (min); Area %=4.27; 98.84.

Intermediate 1.5: Methyl 4-(1-piperidinyl)pyrido[3,2-d]pyrimidine-6-carboxylate (Scheme 8)

To a round-bottom flask were added palladium (540 mg; 0.51 mmol; 0.05 eq.) isopropanol (90 mL). Ar was bubbled in this mixture. A degazed ammonium formate solution in water (2.56 g, 40.6 mmol, 4 eq., in 4 mL of water) was added, followed by methyl 2,8-dichloro-4-(1-piperidinyl)pyrido[3,2-d]pyrimidine-6-carboxylate (Intermediate 1.4) (3.46 g; 10.5 mmol; 1 eq.) and degazed isopropanol (10 mL). After 30 min, a second batch of ammonium formate was added as solution in water (2.56 g, 40.6 mmol, 4 eq., in 4 mL of water). Finally, after additional 30 min, another 8 equivalents of ammonium formate in water were (5.12 g, 81.2 mmol, 8 eq., in 8 mL of water). The mixture was then stirred at rt. overnight and filtered through celite. The filtrate was evaporated. The crude product was dissolved in DCM and washed with water and brine. Organic phase was dried over magnesium sulfate, filtered and evaporated to give methyl 4-(1-piperidinyl)pyrido[3,2-d]pyrimidine-6-carboxylate (2.29 g; 83%) (Intermediate 1.5), as a yellow solid in 92.9% HPLC purity. This product was used in the next step without further purification.

Amount: 2.29 g; Yield: 82%; Formula: $C_{14}H_{16}O_2N_4$; 1H NMR (DMSO-d6) δ 1.70 (sl, 6H), 3.92 (s, 3H), 4.42 (sl, 4H), 8.19 (d, J=9 Hz, 1H), 8.30 (d, J=9 Hz, 1H), 8.52 (s, 1H); HPLC ($H_2O$ TFA 0.1%-ACN TFA 0.05%): Rt (min); Area %=1.83; 92.88; LC-MS: M/Z ESI: Rt (min) 1.58; 273.10 (M+1).

Intermediate 1.6: [4-(1-piperidinyl)pyrido[3,2-d]pyrimidin-6-yl]methanol (Scheme 6)

Methyl 4-(1-piperidinyl)pyrido[3,2-d]pyrimidine-6-carboxylate (Intermediate 1.5) (4.4 g; 16.2 mmol; 1 eq.) was dissolved in THF (176 mL) and the solution was cooled down to −35° C. (internal temperature). Lithium aluminum hydride (8.1 mL; 1.00 M; 8.1 mmol; 0.50 eq.) was added dropwise. After 2 h30 at −35° C. the reaction was complete. Water (8.1 mL) was added and the temperature was allowed to warm up to rt. After addition of MeOH (8 mL), the mixture was filtered through Celite, and widely rinsed with DCM/MeOH 1:1 mixture. Solvents were removed under reduced pressure to give [4-(1-piperidinyl)pyrido[3,2-d]pyrimidin-6-yl]methanol (Intermediate 1.6) (3.99 g; quantitative yield) in 92.9% HPLC purity. This product was used in the next step without further purification. Amount: 3.99 g; Yield: 100%; Formula: $C_{13}H_{16}ON_4$; 1H NMR (DMSO-d6) δ 1.64 (m, 6H), 4.32 (sl, 4H), 4.66 (s, 2H), 7.86 (d, J=9 Hz, 1H), 8.06 (d, J=9 Hz, 1H), 8.44 (s, 1H); LC-MS: M/Z ESI: Rt (min) 1.24; 245.08 (M+1); HPLC ($H_2O$ TFA 0.1%-ACN TFA 0.05%): Rt (min); Area %=1.39; 92.88.

Intermediate 1.7: 4-(1-piperidinyl)pyrido[3,2-d]pyrimidine-6-carbaldehyde (Scheme 6)

[4-(1-piperidinyl)pyrido[3,2-d]pyrimidin-6-yl]methanol (Intermediate 1.6) (3.95 g; 16.2 mmol; 1.00 eq.) was dissolved in DCM (160 mL). The solution was cooled down to 0° C. and manganese oxide (16.5 g; 0.162 mol; 10 eq.) was added. The reaction was stirred 5 min at 0° C. then overnight at rt. To complete the conversion, $MnO_2$ was added after 12 hours and 20 hours (two batches of 4.96 g; 48.48 mmol; 3 eq.). After 20 hours, the reaction was complete. MeOH (100 mL) was added and the mixture was filtered through Celite, and widely rinsed with DCM/MeOH 1:1 mixture. Solvents were removed under reduced pressure to give 4-(1-piperidinyl)pyrido[3,2-d]pyrimidine-6-carbaldehyde (Intermediate 1.7). This product was used in the next step without further purification. Amount: 4.1 g; Formula: $C_{13}H_{14}ON_4$; HPLC Purity: 58.84%; LC-MS: M/Z ESI: Rt (min) 1.53; 243.06 (M+1); HPLC ($H_2O$ TFA 0.1%-ACN TFA 0.05%): Rt (min); Area %=1.39; 58.84. 1H NMR (DMSO-d6) δ 9.95 (s, 1H), 8.52 (s, 1H), 8.16 (m, 2H), 4.46 (l, 4H), 1.70 (l, 6H).

Intermediate 2.1: 4-(4-fluoro-piperidin-1-yl)-pyrido[3,2-d]pyrimidine-6-carbaldehyde (Schemes 6 and 8)

The title compound was obtained using 4-fluoro-piperidine following the general procedure described for the synthesis of intermediate 1.7 (Schemes 5 and 7). Amount: 4.15 g; Formula: $C_{13}H_{13}FON_4$; HPLC Purity: 89.16%; LC-MS: M/Z ESI: Rt (10 min) 2.26; 261.08 (M+1); HPLC ($H_2O$ TFA 0.1%-ACN TFA 0.05%): Rt (min); Area %=1.19; 89.16; 1H NMR (DMSO-d6) δ 10.01 (s, 1H), 8.60 (s, 1H), 8.23 (m, 2H), 5.00 (m, 1H), 4.51 (l, 4H), 1.91 (l, 4H).

Intermediate 3.1: 4-(4-(trifluoromethyl)-piperidin-1-yl)-pyrido[3,2-d]pyrimidine-6-carbaldehyde (Schemes 6 and 8)

The title compound was obtained using 4-trifluoromethyl-piperidine following the general procedure described for the synthesis of intermediate 1.7 (Schemes 5 and 7). Amount: 4.8 g; Formula: $C_{14}H_{13}OF_3N_4$; HPLC Purity: 67.12%; LC-MS: M/Z ESI: Rt (3 min) 1.75; 311.04 (M+1); HPLC ($H_2O$ TFA 0.1%-ACN TFA 0.05%): Rt (min); Area %=1.89; 67.12; 1H NMR (DMSO-d6) δ 10.03 (s, 1H), 8.62 (s, 1H), 8.18 (s, 2H), 3.22 (t, 2H), 2.48 (m, 2H), 2.08 (d, 2H), 1.80 (m, 3H).

Intermediate 4.1: 6-Chloro-pyridine-2,3-diamine (Scheme 10)

2-amino-3-nitro-6-chloropyridine (3 g, 17.3 mmol, 1 eq.) was dissolved in THF (50 mL) at rt. Tin chloride dihydrate (15.6 g, 70 mmol, 4 eq.) pre-dissolved with $HCl_{cc}$ (5 mL) was added slowly and reaction mixture stirred at rt for 4 hours. When thereaction was finished, reaction mixture was cooled down to 0° C. and treated with sodium hydroxide 5M (12 mL) until pH 14 and the corresponding compound extracted with ethyl acetate. Organic phases were dried with magnesium sulfate, evaporated under vacuum and resulting crude material purified by flash chromatography using cyclohexane/ethyl acetate (1/1) to give 1.5 g of a red oil (Intermediate 4.1). Amount: 1.5 g; Yield: 60%; Formula: $C_5H_6N_3Cl$; HPLC Purity: 98%; HPLC ($H_2O$ TFA 0.1%-ACN TFA 0.05%): Rt (min); Area %=0.5 min; 98%; 1H NMR (DMSO-d6) δ 6.67 (d, 1H, H5, J=8 Hz), 6.36 (d, 1H, H4, J=8 Hz), 5.78 (m, 2H, $NH_2$), 4.75 (m, 2H, $NH_2$); LC-MS: M/Z ESI: Rt (min) 0.1 min, 144.0 (M+1).

Intermediate 4.2: 6-Chloro-pyrido[2,3-b]pyrazine (Scheme 10)

6-chloro-2,3-pyridinediamine (Intermediate 4.1) (1 g, 6.96 mmol, 1 eq.) was dissolved in THF (15 mL). Glyoxal (0.84 mL, 18.1 mmol, 2.5 eq.) was added and reaction mixture stirred at rt for 2 hours. Reaction was monitored by RP-HPLC. THF was evaporated, residue re-dissolved in ethyl acetate (30 mL). Organic phases washed twice with saturated $Na_2CO_3$, dried with magnesium sulfate and evaporated under vacuum to give 1.15 g of the expected compound as a white solid (Intermediate 4.2). Amount: 1.15 g; Yield: 100%; Formula: $C_7H_4N_3Cl$; HPLC Purity: 98%; HPLC ($H_2O$ TFA 0.1%-ACN TFA 0.05%): Rt (min); Area %=1.2 min; 98%; 1H NMR (CDCl$_3$) δ 9.0 (s, 1H), 8.88 (s, 1H), 8.36 (d, 1H, J=8 Hz), 7.67 (d, 1H, J=8 Hz); LC-MS: M/Z ESI: Rt (min) 0.68 min, 167.0 (M+1).

Intermediate 4.3: 6-Vinyl-pyrido[2,3-b]pyrazine (Scheme 10)

6-chloropyrido[2,3-b]pyrazine (Intermediate 4.2) (3 g, 18.12 mmol, 1.00 eq.) was dissolved in THF (150 mL) and degassed with nitrogen at rt for 10 minutes. Tetrakis (triphenylphosphine)palladium(0) (1.46 g, 1.27 mmol, 0.07 eq.) and vinyltributylstannane (7.47 mL, 23.5 mmol, 1.3 eq.) were added and reaction mixture was stirred at 65° C. for 3 hours. THF was evaporated and crude purified directly by flash chromatography using cyclohexane/ethyl acetate (8/2) to give 2.3 g of the expected compound (Intermediate 4.3) as an orange oil. Amount: 2.3 g; Yield: 81%; Formula: $C_9H_7N_3$; HPLC Purity: 98%; HPLC ($H_2O$ TFA 0.1%-ACN TFA 0.05%): Rt (min); Area %=1.32 min; 98%; 1H NMR (DMSO-d6) δ 9.10 (s, 1H), 8.98 (s, 1H), 8.46 (d, 1H, J=8 Hz), 7.95 (d, 1H, J=8 Hz), 6.90 (dd, 1H, $J_{trans}$=17 Hz, $J_{cis}$=10 Hz), 6.50 (dd, 1H, $J_{trans}$=17 Hz, $J_{gem}$=1.5 Hz), 5.80 (dd, 1H, $J_{cis}$=10 Hz, $J_{gem}$=1.5 Hz). LC-MS: M/Z ESI: Rt (min) 0.78 min, 158.13 (M+1).

Intermediate 4.4: Pyrido[2,3-b]pyrazine-6-carbaldehyde (Scheme 9)

6-vinylpyrido[2,3-b]pyrazine (Intermediate 4.3) (1 g, 6.37 mmol, 1 eq.) was dissolved in methanol (20 mL) and cooled down to –70° C. A gentle flux of a mixture of oxygen/ozone was then bubbled through for 20 minutes. The reaction was monitored by TLC using cyclohexane/ethyl acetate (8/2). When the reaction was finished, dimethylsulfide (0.1 mL) was added and reaction was left at rt for 30 minutes. Methanol was evaporated under vacuum and 600 mg of pyrido[2,3-b]pyrazine-6-carbaldehyde was recovered. Crude material was analyzed without further purification (Intermediate 4.4). Amount: 0.60 g; Yield: 60%; Formula: $C_8H5N_3O$; HPLC Purity: 90%; HPLC ($H_2O$ TFA 0.1%-ACN TFA 0.05%): Rt (min); Area %=0.90 min; 90%; 1H NMR (DMSO-d6) δ 10.1 (l, 1H), 9.05 (s, 1H), 8.95 (s, 1H), 8.70 (d, 1H, J=8 Hz), 8.20 (d, 1H, J=8 Hz); LC-MS: M/Z ESI: Rt (min) 0.76 min, 158.13 (M+1).

Intermediate 5.1: 5-Methyl-2-trimethylsilanyl-furo[3,2-b]pyridine (Scheme 11)

To a degased solution of 6-iodo-2-picolin-5-ol (855 mg; 3.64 mmol; 1.00 eq.) in triethylamine (20.00 mL) were added (trimethylsilyl)acetylene (1 g; 10.19 mmol; 2.80 eq.), cuprous iodide (90.07 mg; 0.47 mmol; 0.13 eq.) and dichlorobis(triphenyl phosphine)palladium(II) (229.82 mg; 0.33 mmol; 0.09 eq.). The solution was heated under reflux. After 3 h, the reaction was complete, and allowed to cool down to rt. The solution was filtered over celite (washed with AcOEt and MeOH). The solvents were removed. AcOEt and water were added and the combined organic layers were dried over magnesium sulfate, filtered and concentrated to give the expected compound. The crude was purified by short flash chromatography using cyclohexane then AcOEt/Cyclohexane 20/80 to afford 603 mg of the desired compound as a solid (Intermediate 5.1). Amount: 603 mg; Yield: 81%; Formula: C11H15NOSi; HPLC Purity: 93.14%; HPLC (H₂O TFA 0.1%-ACN TFA 0.05%): Rt (min); Area %=2.17 min; 93.14%; 1H NMR (CDCl3) δ 7.65 (d, 1H, J=8.5 Hz), 7.10 (s, 1H), 7.06 (d, 1H, J=8.5 Hz), 2.67 (s, 3H), 0.36 (s, 9H); LC-MS: M/Z ESI: Rt (min) 1.89 min, 206.06 (M+1).

Intermediate 5.2: 2-Trimethylsilanyl-furo[3,2-b]pyridine-5-carbaldehyde (Scheme 11)

To a solution of 5-methyl-2-(trimethylsilyl)furo[3,2-b]pyridine (Intermediate 5.1) (600 mg; 2.92 mmol; 1 eq.) in 1,2-dichlorobenzene (12 mL) was added selenium dioxide (486 mg; 4.38 mmol; 1.5 eq.). The reaction mixture was heated under microwave at 220° C. for 6 h. The solution was concentrated under vacuum. Et₂O was added and the black solid was filtered. The filtrate was concentrated and purified by flash chromatography using cyclohexane then cyclohexane/AcOEt 90/10 affording a solid (Intermediate 5.2). Amount: 130 mg; Yield: 20%; Formula: C11H13NO2Si; HPLC Purity: 81.8%; HPLC (H₂O TFA 0.1%-ACN TFA 0.05%): Rt (min); Area %=3.84 min; 81.83%; 1H NMR (CDCl₃) δ 10.19 (s, 1H), 7.99 (d, 1H, J=8.50 Hz), 7.89 (d, 1H, J=8.50 Hz), 7.27 (s, 1H), 0.40 (s, 9H); LC-MS: M/Z ESI: Rt (min) 1.86 min, 220 (M+1).

General Procedures for the Synthesis of Intermediates 6 to 16.3:

General Procedure I for Substitution of Intermediate P5d with $R^2NH_2$ (Scheme 12):

A solution of 2,6-dibromo-3-nitropyridine (Intermediate 6 of formula P5d wherein Hal is Br and $R^1$ is H) (1 eq.), arylamine (1.0-1.2 eq.), and triethylamine (2 eq.) in ethanol (5 mL/mmol) is stirred for 48 h at ambient temperature. Filtration of the resulting precipitate furnishes the respective substitution product with high purity.

General Procedure II for Reduction (Scheme 12):

A mixture of the bromopyridine (1 eq.), indium powder (3-6 eq.), saturated aqeous ammonium chloride (8 ml/mmol), and ethanol (20 ml/mmol) is sirred under reflux for 4 h. Filtration through Celite® and concentration of the filtrate in vacuo is followed by basic extraction. The organic layer is dried over sodium sulfate and concentrated in vacuo. The resulting corresponding diaminopyridine is used in the next step without further purification.

General Procedure III for Cyclization (Scheme 12):

A mixture of diaminopyridine (1 eq.), formamidine acetate (3-5 eq.), and 2-methoxyethanol (30 ml/mmol) is sirred under reflux for 15 h. The mixture is concentrated in vacuo and chromatographically purified (EtOAc/hexane gradient) to yield the corresponding bromoimidazo[4,5-b]pyridine.

General Procedure IV for Coupling (Scheme 12):

A solution of bromoimidazo[4,5-b]pyridine (1 eq.), tributyl(vinyl)tin (1.5-3 eq.), and tetrakis(triphenylphosphine)palladium(0) (0.1 eq.) in toluene (deoxygenated with N₂, 20 ml/mmol ml) is stirred under reflux for 4 h. Concentration in vacuo and chromatographic purification (EtOAc/hexane gradient) yields the corresponding vinylimidazo[4,5-b]pyridine.

General Procedure V for Oxidation of Intermediate 4 (Scheme 13):

A mixture of vinylimidazo[4,5-b]pyridine (1 eq.), osmium tetroxide (0.1 eq.), sodium periodate (3-4 eq.), 1,4-dioxane (30 ml/mmol), and water (25 ml/mmol) is stirred for 15-30 min at ambient temperature. The resulting slurry is diluted with even amounts of water and ethyl acetate. After filtration through Celite®, the organic phase is dried over sodium sulfate, concentrated in vacuo and purified via flash chromatography to yield the respective fonnylimidazo[4,5-b]pyridine.

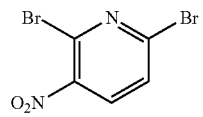

Intermediate 6: 2,6-dibromo-3-nitropyridine (Scheme 12)

A mixture of commercially available 2,6-dichloro-3-nitropyridine (10.0 g; 51.8 mmol) and 33 w % HBr/AcOH (120 mL) is heated at 80° C. for 3 h. The solution is concentrated in vacuo, the resulting residue is taken into EtOAc and ished with saturated aqueous sodium bicarbonate. The organic phase is dried over sodium sulfate and concentrated in vacuo. The resulting product 14.4 g (99%) is used without further purification (Intermediate 6). GC/MS: 94% purity, $t_R$ 7.56 min ($t_{R(SM)}$ 6.93 min), m/z ($C_5H_2Br_2N_2$) 280/282/284 (M, 38), 222/224/226 (35), 76 (100) Finnegan LCQ.

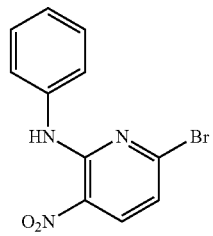

Intermediate 7.1: N-(5-bromo-2-nitrophenyl)-N-phenylamine (Scheme 12)

The title compound is obtained from 2,6-dibromo-3-nitropyridine (Intermediate 6) and aniline in 95% yield following general procedure I (Intermediate 7.1). GC/MS: 99% purity, $t_R$ 9.28 min ($t_{R(SM: nitropyridine)}$ 7.62 min), m/z 293/295 (M, 12), 168 (25), 140 (25), 77 (100) Finnegan LCQ.

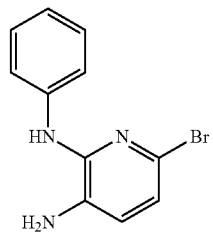

Intermediate 7.2: 6-Bromo-$N^2$-phenylpyridine-2,3-diamine (Scheme 12)

The title compound is obtained from N-(5-bromo-2-nitrophenyl)-N-phenylamine (Intermediate 7.1) in 97% following general procedure II. GC/MS: 99% purity, $t_R$ 9.69 min ($t_{R(SM)}$ 9.27 min), m/z 263/265 (M, 45), 183 (19), 104 (18), 92 (23), 77 (42) Finnegan LCQ.

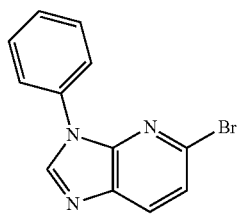

Intermediate 7.3:
5-Bromo-3-phenyl-3H-imidazo[4,5-b]pyridine
(Scheme 12)

The title compound is obtained from 6-Bromo-$N^2$-phenylpyridine-2,3-diamine (Intermediate 7.2) in 71% yield following general procedure III. GC/MS: 99% purity, $t_R$ 9.23 min ($t_{R(SM)}$ 9.72 min), m/z 273/275 (M, 55), 194 (36), 167 (30), 77 (100) Finnegan LCQ.

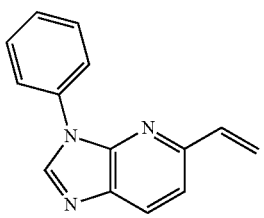

Intermediate 7.4:
3-Phenyl-5-vinyl-3H-imidazol[4,5-b]pyridine
(Scheme 12)

The title compound is obtained from 5-bromo-3-phenyl-3H-imidazo[4,5-b]pyridine (Intermediate 7.3) in 92% yield following general procedure IV. GC/MS: 97% purity, $t_R$ 8.94 min ($t_{R(SM)}$ 9.23 min), m/z 221 (M, 100), 77 (58) Finnegan LCQ.

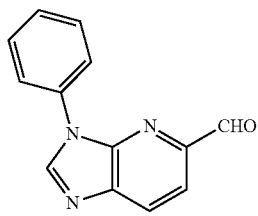

Intermediate 7.5:
3-Phenyl-3H-imidazo[4,5-b]pyridine-5-carbaldehyde
(Scheme 13)

The title compound is obtained from 3-phenyl-5-vinyl-3H-imidazo[4,5-b]pyridine (Intermediate 7.4) in 36% yield following general procedure V. GC/MS: 97% purity, $t_R$ 9.20 min ($t_{R(SM)}$ 9.04 min), m/z 223 (M, 55), 195 (63), 77 (100) Finnegan LCQ.

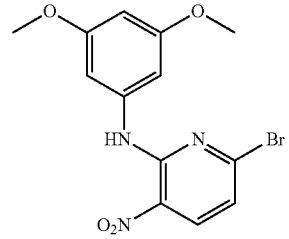

Intermediate 8.1: N-(5-Bromo-2-nitrophenyl)-N-(3, 5-dimethoxyphenyl)amine (Scheme 12)

The title compound is obtained from commercially available 2,6-dibromo-3-nitropyridine and 3,5-dimethoxyaniline in 85% yield following general procedure I. HPLC (over 10 min 10-85% MeCN/100 mM aq. NaOAc): 98% purity, $t_R$ 10.12 min ($t_{R(SM:\ nitropyridine)}$ 7.98 min). GC/MS: 99% purity, $t_R$ 10.88 min ($t_{R(SM:\ nitropyridine)}$ 7.50 min), m/z 253/255 (M, 100), 228 (72), 122 (41), 77 (53) Finnegan LCQ. $^1$H-NMR (400 MHz, DMSO-$d_6$): δ 10.04 (s, 1H), 8.42 (d, 1H), 7.19 (d, 1H), 6.94 (s, 2H), 6.33 (s, 1H), 3.76 (s, 6H) ppm.

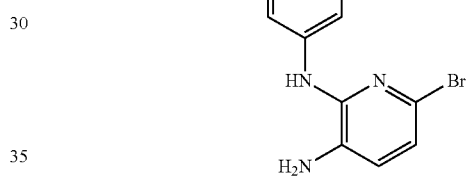

Intermediate 8.2: 6-Bromo-$N^2$-(3,5-dimethoxyphenyl)pyridine-2,3-diamine (Scheme 12)

The title compound is obtained from N-(5-Bromo-2-nitrophenyl)-N-(3,5-dimethoxyphenyl)amine (Intermediate 8.1) in 93% yield using genral procedure II. HPLC (over 10 min 10-85% MeCN/100mM aq. NaOAc): 96% purity, $t_R$ 8.38 min ($t_{R(SM)}$ 10.12 min). GC/MS: 97% purity, $t_R$ 11.47 min ($t_{R(SM)}$ 10.15 min), m/z 323/325 (M, 100), 310/308 (33), 292/294 (39) Finnegan LCQ.

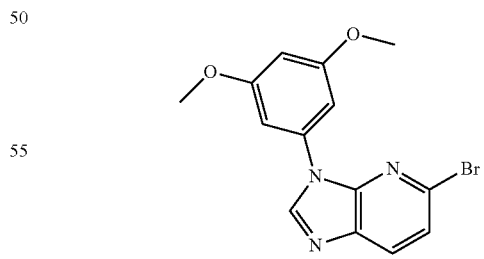

Intermediate 8.3: 5-Bromo-3-(3,5-dimethoxyphenyl)-3H-imidazo[4,5-b]pyridine (Scheme 12)

The title compound is obtained from 6-Bromo-$N^2$-(3,5-dimethoxyphenyl)pyridine-2,3-diamine (Intermediate 8.2) in 43% yield following general procedure III. HPLC (over 10 min 10-85% MeCN/100 mM aq. NaOAc): 98% purity, $t_R$ 8.51 min ($t_{R(SM)}$ 8.40 min). GC/MS: 98% purity, $t_R$ 10.56 min ($t_{R(SM)}$ 11.47 min), m/z 333/335 (M, 79), 207 (100) Finnegan LCQ.

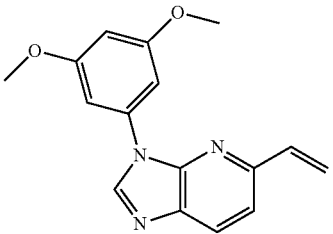

Intermediate 8.4: 3-(3,5-Dimethoxyphenyl)-5-vinyl-3H-imidazo[4,5-b]pyridine (Scheme 12)

The title compound is obtained from 5-bromo-3-(3,5-dimethoxyphenyl)-3H-imidazo[4,5-b]pyridine (Intermediate 8.3) in 57% yield following general procedure IV. HPLC (over 10 min 10-85% MeCN/100 mM aq. NaOAc): 99% purity, $t_R$ 8.39 min ($t_{R(SM)}$ 8.51 min). GC/MS: 99% purity, $t_R$ 10.36 min ($t_{R(SM)}$ 10.56 min), m/z 281 (M, 100) Finnegan LCQ.

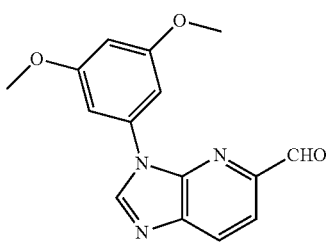

Intermediate 8.5: 3-(3,5-Dimethoxyphenyl)-3H-imidazo[4,5-b]pyridine-5-carbaldehyde (Scheme 13)

The title compound is obtained from 3-(3,5-dimethoxyphenyl)-5-vinyl-3H-imidazo[4,5-b]pyridine (Intermediate 8.4) in 56% yield following general procedure V. HPLC (over 10 min 10-85% MeCN/100 mM aq. NaOAc): 98% purity, $t_R$ 7.26 min ($t_{R(SM)}$ 8.39 min). GC/MS: 99% purity, $t_R$ 10.32 min ($t_{R(SM)}$ 10.36 min), m/z 283 (M, 100) Finnegan LCQ.

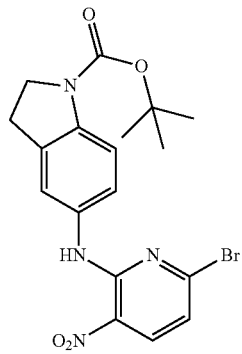

Intermediate 9.1: Tert-butyl 5-[(5-bromo-2-nitrophenyl)amino]indoline-1-carboxylate (Scheme 12)

The title compound is obtained from 2,6-dibromo-3-nitropyridine and tent-butyl 5-aminoindoline-1-carboxylate (derived from commercially available 5-nitroindoline via N-Boc protection and subsequent reduction of the nitro group with $H_2$/Pd/C in MeOH/EtOAc) in 97% yield following general procedure I. HPLC (over 10 min 10-85% MeCN/0.1% TFA/$H_2O$): 99% purity, $t_R$ 10.35 min ($t_{R(SM:\ nitropyridine)}$ 6.79 min). $^1$H-NMR (400 MHz, CDCl$_3$): δ 10.16 (s, 1H), 8.31 (d, 1H), 7.86 (br s, 0.4H), 7.49 (s, 1H), 7.45 (br s, 0.6H), 7.31 (d, 1H), 6.92 (d, 1H), 4.03 (br t, 2H), 3.14 (t, 2H), 1.56 (s, 9H) ppm. MS (ESI) m/z ($C_{18}H_{19}O_4BrN_4$) 435.2/437.1 (M+1, 100) Finnegan LCQ.

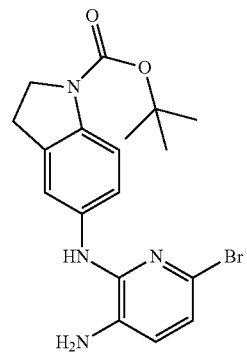

Intermediate 9.2: Tert-butyl 5-[(3-amino-6-bromopyridin-2-yl)amino]indoline-1-carboxylate (Scheme 12)

The title compound is obtained from tert-butyl 5-[(5-bromo-2-nitrophenyl)amino]indoline-1-carboxylate (Intermediate 9.1) in 96% yield following general procedure II. HPLC (over 10 min 10-85% MeCN/100 mM aq. NaOAc): 98% purity, $t_R$ 9.86 min ($t_{R(SM)}$ 11.66 min). MS (ESI) m/z ($C_{18}H_{21}BrN_4O_2$) 405.1/407.0 (M+1, 100), 349.1/351.1 (82) Finnegan LCQ.

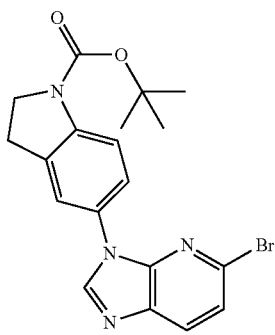

Intermediate 9.3: Tert-butyl 5-(5-bromo-3H-imidazo[4,5-b]pyridin-3-yl)indoline-1-carboxylate (Scheme 12)

The title compound is obtained from tert-butyl 5-[(3-amino-6-bromopyridin-2-yl)amino]indoline-1-carboxylate (Intermediate 9.2) in 91% yield following general procedure III. HPLC (over 10 min 10-85% MeCN/100 mM aq. NaOAc): 97% purity, $t_R$ 10.08 min ($t_{R(SM)}$ 9.85 min). MS (ESI) m/z ($C_{19}H_{19}BrN_4O_2$) 415.0/416.9 (M+1, 91), 359.1/361.0 (100), 315.1/317.2 (51) Finnegan LCQ.

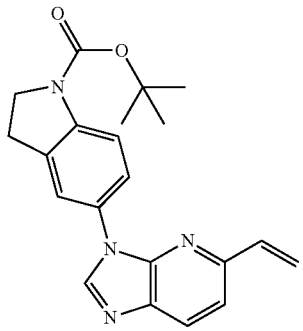

Intermediate 9.4: Tert-butyl 5-(5-vinyl-3H-imidazo [4,5-b]pyridin-3-yl)indoline-1-carboxylate (Scheme 12)

The title compound is obtained from tert-butyl 5-(5-bromo-3H-imidazo[4,5-b]pyridin-3-yl)indoline-1-carboxylate (Intermediate 9.3) in 94% yield following general procedure IV. HPLC (over 10 min 10-85% MeCN/0.1% TFA/$H_2O$): 96% purity, $t_R$ 7.21 min ($t_{R(SM)}$ 8.51 min). $^1$H-NMR (400 MHz, $CDCl_3$) δ 8.21 (s, 1H), 8.04 (d, 1H), 7.98 (br s, 0.5H), 7.56 (s, 1H), 7.55 (br s, 0.5H), 7.48 (d, 1H), 7.35 (d, 1H), 6.89 (dd, 1H), 6.19 (d, 1H), 5.42 (d, 1H), 4.05 (t, 2H), 3.18 (t, 2H), 1.55 (s, 9H) ppm.

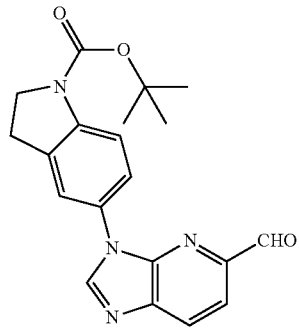

Intermediate 9.5: Tert-butyl 5-(5-formyl-3H-imidazo [4,5-b]pyridin-3-yl)indoline-1-carboxylate (Scheme 13)

The title compound is obtained from tert-butyl 5-(5-vinyl-3H-imidazo[4,5-b]pyridin-3-yl)indoline-1-carboxylate (Intermediate 9.4) in 69% yield following general procedure V. HPLC (over 10 min 10-85% MeCN/0.1% TFA/$H_2O$): 96% purity, $t_R$ 7.31 min ($t_{R(SM)}$ 7.21 min).

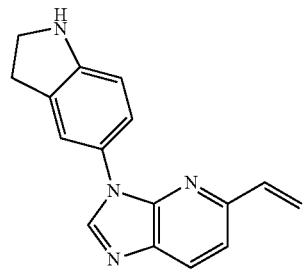

Intermediate 10.1: 3-(2,3-dihydro-1H-indol-5-yl)-5-vinyl-3H-imidazo[4,5-b]pyridine (Scheme 12)

A mixture of tert-butyl 5-(5-vinyl-3H-imidazo[4,5-b]pyridin-3-yl)indoline-1-carboxylate (Intermediate 9.4) (9.50 g, 26.21 mmol) (intermediate 9.4), 4 M HCl in 1,4-dioxane (200 ml), 2-propanol (30 ml), and dioxane (50 ml) is stirred for 1.5 h at ambient temperature. The mixture is concentrated to dryness to furnish 9.50 g (98% yield) of the trihydrochloride salt of the corresponding free amine. HPLC (over 10 min 10-85% MeCN/100 mM aq. NaOAc): 99% purity, $t_R$ 6.64 min ($t_{R(SM)}$ 10.06 min). $^1$H-NMR (400 MHz, methanol-$d_4$) δ 9.97 (s, 1H), 8.34 (d, 1H), 8.12 (d, 1H), 8.04 (d, 1H), 7.85 (d, 1H), 7.82 (d, 1H), 7.63 (m, 1H), 7.54 (m, 1H), 6.98 (dd, 1H), 6.37 (d, 1H), 5.63 (d, 1H), 4.02 (t, 2H), 3.52 (t, 2H) ppm. MS (ESI) m/z ($C_{16}H_{14}N_4$) 263.2 (M+1, 100), 219.2 (32) Finnegan LCQ.

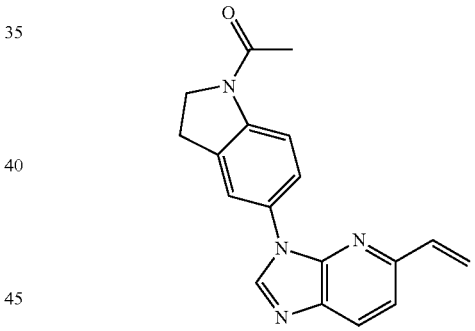

Intermediate 10.2: 3-(1-acetyl-2,3-dihydro-1H-indol-5-yl)-5-vinyl-3H-imidazo[4,5-b]pyridine (Scheme 12)

A mixture of 3-(2,3-dihydro-1H-indol-5-yl)-5-vinyl-3H-imidazo[4,5-b]pyridine (Intermediate 10.1) (150.0 mg, 0.57 mmol), glacial acetic acid (39.3 µl, 0.69 mmol), N-ethyl-N'-(3-dimethylaminopropyl)carbodiimide hydrochloride (175.4 mg, 0.91 mmol), 4-dimethylaminopyridine (419.2 mg, 3.43 mmol), and dichloromethane (10 ml) is stirred for 24 h at ambient temperature. The mixture is successively extracted with saturated aqueous ammonium chloride and saturated aqueous sodium bicarbonate. The organic layer is dried over sodium sulfate and concentrated in vacuo to render 139.1 mg (80%) of the respective amide. HPLC (over 10 min 10-85% MeCN/100 mM aq. NaOAc): 99% purity, $t_R$ 6.43 min ($t_{R(SM)}$ 6.64 min). GC/MS: 96% purity, $t_R$ 13.98 min, m/z 304 (M, 58), 262 (100), 207 (62) Finnegan LCQ.

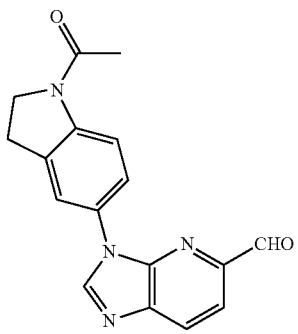

Intermediate 10.3: 3-(1-acetyl-2,3-dihydro-1H-indol-5-yl)-3H-imidazo[4,5-b]pyridine-5-carbaldehyde (Scheme 13)

The title compound is obtained from 3-(1-acetyl-2,3-dihydro-1H-indol-5-yl)-5-vinyl-3H-imidazo[4,5-b]pyridine (Intermediate 10.2) in 44% yield following general procedure V. HPLC (over 10 min 10-85% MeCN/100 mM aq. NaOAc): 95% purity, $t_R$ 5.38 min ($t_{R(SM)}$ 6.43 min). GC/MS: $t_R$ 14.98 min ($t_{R(SM)}$ 13.98 min), m/z 306 (M, 60), 264 (100) Finnegan LCQ.

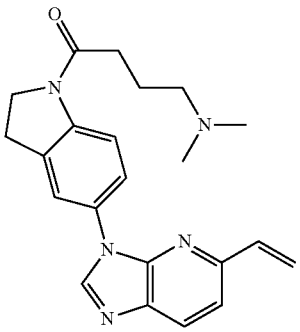

Intermediate 11.1: N,N-dimethyl-N-{4-oxo-4-[5-(5-vinyl-3H-imidazo[4,5-b]pyridin-3-yl)-2,3-dihydro-1H-indol-1-yl]butyl}amine (Scheme 12)

A mixture of 3-(2,3-dihydro-1H-indol-5-yl)-5-vinyl-3H-imidazo[4,5-b]pyridine (48.0 mg, 0.14 mmol) (Intermediate 10.1), 4-(dimethylamino)butyric acid hydrochloride (36.3 mg, 0.21 mmol), N-ethyl-N'-(3-dimethylaminopropyl)carbodiimide hydrochloride (54.9 mg, 0.29 mmol), 4-dimethylaminopyridine (122.5 mg, 1.00 mmol), and dichloromethane (8 ml) is stirred for 24 h at ambient temperature. The mixture is successively extracted with saturated aqueous ammonium chloride and saturated aqueous sodium bicarbonate. The organic layer is dried over sodium sulfate and concentrated in vacuo to render 50.4 mg (94%) of the respective amide. HPLC (over 10 min 10-85% MeCN/100 mM aq. NaOAc): 92% purity, $t_R$ 6.27 min ($t_{R(SM)}$ 6.61 min).

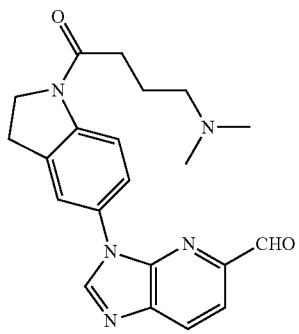

Intermediate 11.2: 3-{1-[4-(dimethylamino)butanoyl]-2,3-dihydro-1H-indol-5-yl}-3 H-imidazo[4,5-b]pyridine-5-carbaldehyde (Scheme 13)

The title compound is obtained from N,N-dimethyl-N-{4-oxo-4-[5-(5-vinyl-3H-imidazo[4,5-b]pyridin-3-yl)-2,3-dihydro-1H-indol-1-yl]butyl}amine(Intermediate 11.1) in 45% yield following general procedure V. HPLC (over 10 min 10-85% MeCN/100 mM aq. NaOAc): 94% purity, $t_R$ 5.02 min ($t_{R(SM)}$ 6.27 min).

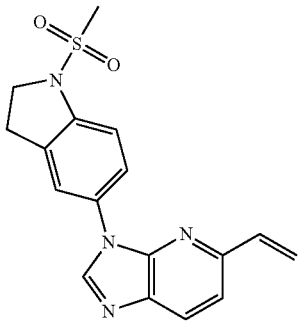

Intermediate 12.1: 3-[1-(methylsulfonyl)-2,3-dihydro-1H-indol-5-yl]-5-vinyl-3H-imidazo[4,5-b]pyridine (Scheme 12)

A solution of 3-(2,3-dihydro-1H-indol-5-yl)-5-vinyl-3H-imidazo[4,5-b]pyridine (2.53 g, 9.64 mmol) (Intermediate 10.1), methanesulfonyl chloride (1.12 ml, 14.47 mmol), and triethylamine (2.94 ml, 21.22 mmol) in dichloromethane (50 ml) is stirred for 30 min at ambient temperature. The mixture is successively extracted with saturated aqueous ammonium chloride and saturated aqueous sodium bicarbonate. The organic layer is dried over sodium sulfate and concentrated in vacuo to render 3.24 g (99%) of the respective sulfonamide. HPLC (over 10 min 10-85% MeCN/100 mM aq. NaOAc): 92% purity, $t_R$ 7.16 min ($t_{R(SM)}$ 6.64 min). MS (ESI) m/z ($C_{17}H_{16}N_4O_2S$) 341.1 (M+1, 100) Finnegan LCQ.

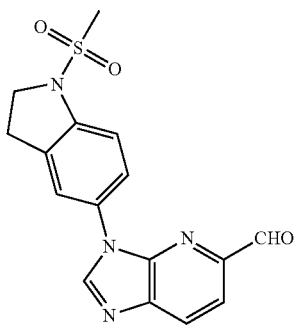

Intermediate 12.2: 3-[1-(methylsulfonyl)-2,3-dihydro-1H-indol-5-yl]-3H-imidazo[4,5-b]pyridine-5-carbaldehyde (Scheme 13)

The title compound is obtained from 3-[1-(methylsulfonyl)-2,3-dihydro-1H-indol-5-yl]-5-vinyl-3H-imidazo[4,5-b]pyridine (Intermediate 12.1) in 60% yield following general procedure V. HPLC (over 10 min 10-85% MeCN/100 mM aq. NaOAc): 98% purity, $t_R$ 6.13 min ($t_{R(SM)}$ 7.16 min).

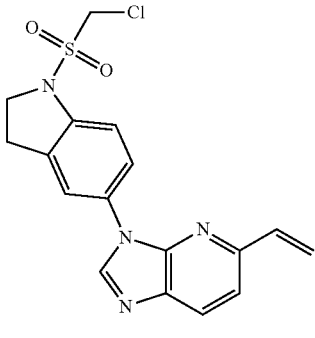

Intermediate 13.1: 3-{1-[(chloromethyl)sulfonyl]-2,3-dihydro-1H-indol-5-yl}-5-vinyl-3H-imidazo[4,5-b]pyridine (Scheme 12)

A solution of 3-(2,3-dihydro-1H-indol-5-yl)-5-vinyl-3H-imidazo[4,5-b]pyridine (2.57 g, 9.80 mmol) (Intermediate 10.1), chloromethanesulfonyl chloride (2.00 ml, 19.59 mmol), and N,N-diisopropylethylamine (11.98 ml, 68.58 mmol) in dichloromethane (100 ml) is stirred for 20 min at ambient temperature. The mixture is successively extracted with saturated aqueous ammonium chloride and saturated aqueous sodium bicarbonate. The organic layer is dried over sodium sulfate and concentrated in vacuo to give 3.61 g (98%) of the respective sulfonamide. HPLC (over 10 min 10-85% MeCN/100 mM aq. NaOAc): 92% purity, $t_R$ 8.05 min ($t_{R(SM)}$ 6.64 min). $^1$H-NMR (400 MHz, DMSO-$d_6$) δ 9.03 (s, 1H), 8.22 (d, 1H), 7.85 (s, 1H), 7.79 (d, 1H), 7.56 (m, 2H), 6.93 (dd, 1H), 6.25 (d, 1H), 5.50 (d, 1H), 5.41 (s, 2H), 4.21 (t, 2H), 3.28 (t, 2H) ppm. MS (ESI) m/z ($C_{17}H_{15}ClN_4O_2S$) 375.0 (M+1, 100) Finnegan LCQ.

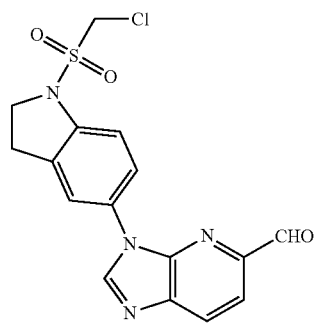

Intermediate 13.2: 3-{1-[(chloromethyl)sulfonyl]-2,3-dihydro-1H-indol-5-yl}-3H-imidazo[4,5-b]pyridine-5-carbaldehyde (Scheme 13)

The title compound is obtained from 3-{1-[(chloromethyp-sulfonyl]-2,3-dihydro-1H-indol-5-yl}-5-vinyl-3H-imidazo[4,5-b]pyridine (Intermediate 13.1) in 86% yield following general procedure V. HPLC (over 10 min 10-85% MeCN/100 mM aq. NaOAc): 97% purity, $t_R$ 7.03 min ($t_{R(SM)}$ 8.05 min). MS (ESI) m/z ($C_{16}H_{13}ClN_4O_3S$) 377.0 (M+1, 100) Finnegan LCQ.

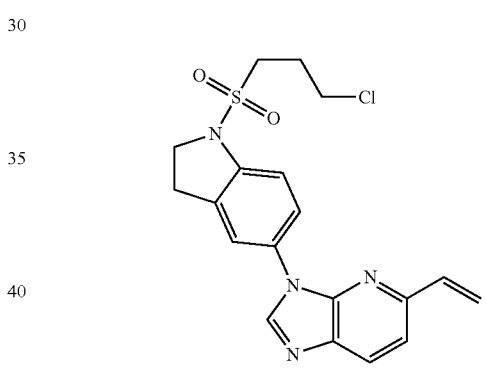

Intermediate 14.1: 3-{1-[(3-chloropropyl)sulfonyl]-2,3-dihydro-1H-indol-5-yl}-5-vinyl-3H-imidazo[4,5-b]pyridine (Scheme 12)

A solution of 3-(2,3-dihydro-1H-indol-5-yl)-5-vinyl-3H-imidazo[4,5-b]pyridine (270 mg, 1.03 mmol) (Intermediate 10.1), 3-chloropropanesulfonyl chloride (0.25 ml, 2.06 mmol), and N,N-diisopropylethylamine (1.08 ml, 6.18 mmol) in dichloromethane (15 ml) is stirred for 10 min at ambient temperature. The mixture is successively extracted with saturated aqueous ammonium chloride and saturated aqueous sodium bicarbonate. The organic layer is dried over sodium sulfate and concentrated in vacuo to render 351 mg (85%) of the respective sulfonamide. HPLC (over 10 min 10-85% MeCN/100 mM aq. NaOAc): 92% purity, $t_R$ 8.44 min ($t_{R(SM)}$ 6.59 min). MS (ESI) m/z ($C_{19}H_{19}ClN_4O_2S$) 403.0 (m, 100), 294.9 (65) Finnegan LCQ.

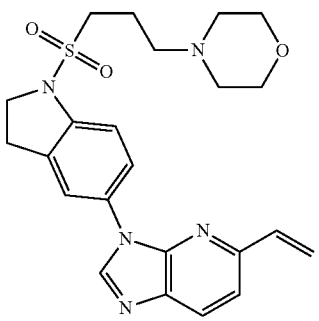

Intermediate 14.2: 3-{1-[(3-morpholin-4-ylpropyl)sulfonyl]-2,3-dihydro-1H-indol-5-yl}-5-vinyl-3H-imidazo[4,5-b]pyridine (Scheme 12)

A mixture of 3-{1-[(3-chloropropyl)sulfonyl]-2,3-dihydro-1H-indol-5-yl}-5-vinyl-3 H-imidazo[4,5-b]pyridine (Intermediate 14.1) (351 mg, 0.87 mmol), morpholine (0.46 ml, 5.23 mmol), potassium iodide (144.6 mg, 0.87 mmol), and N,N-dimethylformamide (10 ml) is stirred for 24 h at ambient temperature. The mixture is extracted with saturated aqueous ammonium chloride and the organic layer is dried over sodium sulfate. Concentration in vacuo furnishes 382 mg (97%) of the respective morpholino derivative. HPLC (over 10 min 10-85% MeCN/100 mM aq. NaOAc): 91% purity, $t_R$ 8.44 min ($t_{R(SM)}$ 8.44 min). $^1$H-NMR (400 MHz, CDCl$_3$) δ 8.32 (s, 1H), 8.09 (d, 1H), 7.68 (s, 1H), 7.55 (m, 2H), 7.41 (d, 1H), 6.90 (dd, 1H), 6.22 (d, 1H), 5.48 (d, 1H), 4.14 (t, 2H), 3.70 (m, 4H), 3.40-3.18 (m, 8H), 2.36 (m, 2H) ppm. MS (ESI) m/z (C$_{23}$H$_{27}$N$_5$O$_3$S) 454.0 (M, 10) Finnegan LCQ.

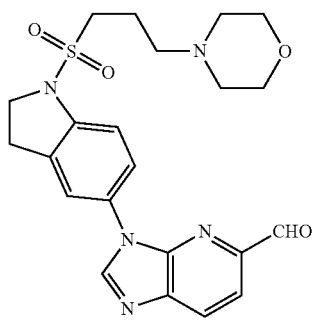

Intermediate 14.3: 3-{1-[(3-morpholin-4-ylpropyl)sulfonyl]-2,3-dihydro-1H-indol-5-yl}-3H-imidazo[4,5-b]pyridine-5-carbaldehyde (Scheme 13)

The title compound is obtained from 3-{1-[(3-morpholin-4-ylpropyl)sulfonyl]-2,3-dihydro-1H-indol-5-yl}-5-vinyl-3H-imidazo[4,5-b]pyridine (Intermediate 14.2) in 82% yield following general procedure V. HPLC (over 10 min 10-85% MeCN/100 mM aq. NaOAc): $t_R$ 7.55 min ($t_{R(SM)}$ 8.44 min). MS (ESI) m/z (C$_{22}$H$_{25}$N$_5$O$_4$S) 456.1 (M+1, 100) Finnegan LCQ.

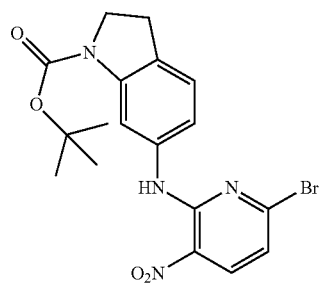

Intermediate 15.1

Tert-butyl 6-[(5-bromo-2-nitrophenyl)amino]indoline-1-carboxylate (Scheme 12)

The title compound is obtained from 2,6-dibromo-3-nitropyridine and tert-butyl 6-aminoindoline-1-carboxylate (derived from commercially available 6-nitroindoline via N-Boc protection and subsequent reduction of the nitro group with H$_2$/Pd/C in MeOH/EtOAc) in 51% yield following general procedure I. HPLC (over 10 min 10-85% MeCN/0.1% TFA/H$_2$O): 99% purity, $t_R$ 10.45 min ($t_{R(SM:\ nitropyridine)}$ 7.98 min). MS (ESI) m/z (C18H$_{19}$O$_4$BrN$_4$) 435.2/437.1 (M+1, 100) Finnegan LCQ.

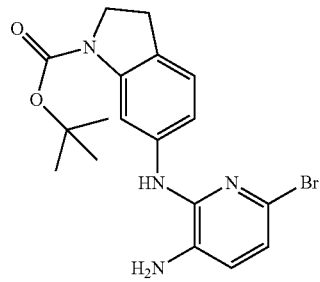

Intermediate 15.2: Tert-butyl 6-[(3-amino-6-bromopyridin-2-yl)amino]indoline-1-carboxylate (Scheme 12)

The title compound is obtained from tert-butyl 6-[(5-bromo-2-nitrophenyl)amino]indoline-1-carboxylate (Intermediate 15.1) in 98% yield following general procedure II. HPLC (over 10 min 10-85% MeCN/100 mM aq. NaOAc): 99% purity, $t_R$ 9.72 min ($t_{R(SM)}$ 11.38 min). MS (ESI) m/z (C$_{18}$H$_{21}$BrN$_4$O$_2$) 426.8/428.9 (M+Na$^+$, 87), 405.1/407.0 (M+H$^+$, 23), 349.1/351.0 (100), 305.1/307.1 (56) Finnegan LCQ.

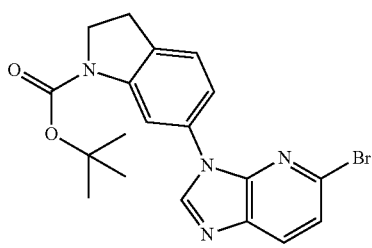

Intermediate 15.3: Tert-butyl 6-(5-bromo-3H-imidazo[4,5-b]pyridin-3-yl)indoline-1-carboxylate (Scheme 12)

The title compound is obtained from tert-butyl 6-[(3-amino-6-bromopyridin-2-yl)amino]indoline-1-carboxylate (Intermediate 15.2) in 76% yield following general procedure III. HPLC (over 10 min 10-85% MeCN/100 mM aq. NaOAc): 99% purity, $t_R$ 9.78 min ($t_{R(SM)}$ 9.72 min). MS (ESI) m/z ($C_{19}H_{19}BrN_4O_2$) 415.0/416.9 (M+1, 74), 359.1/361.0 (100), 315.1/317.2 (51) Finnegan LCQ.

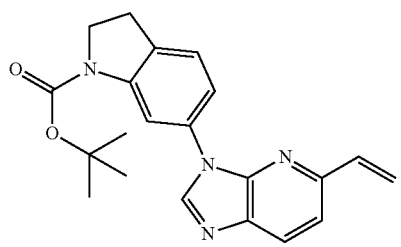

Intermediate 15.4: Tert-butyl 6-(5-vinyl-3H-imidazo[4,5-b]pyridin-3-yl)indoline-1-carboxylate (Scheme 12)

The title compound is obtained from tert-butyl 6-(5-bromo-3H-imidazo[4,5-b]pyridin-3-yl)indoline-1-carboxylate (Intermediate 15.3) in 69% yield following general procedure IV. HPLC (over 10 min 10-85% MeCN/100 mM aq. NaOAc): 99% purity, $t_R$ 9.76 min ($t_{R(SM)}$ 9.78 min). MS (ESI) m/z ($C_{21}H_{21}N_4O_2$) 363.0 (M+1, 100), 307.0 (92) Finnegan LCQ.

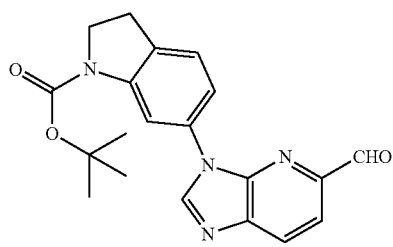

Intermediate 15.5: Tert-butyl 6-(5-formyl-3H-imidazo[4,5-b]pyridin-3-yl)indoline-1-carboxylate (Scheme 13)

The title compound is obtained from tert-butyl 6-(5-vinyl-3H-imidazo[4,5-b]pyridin-3-yl)indoline-1-carboxylate (Intermediate 15.4) in 95% yield following general procedure V. HPLC (over 10 min 10-85% MeCN/100 mM aq. NaOAc): 88% purity, $t_R$ 8.61 min ($t_{R(SM)}$ 9.76 min). MS (ESI) m/z ($C_{20}H_{20}N_4O_3$) 365.1 (M+1, 100) Finnegan LCQ.

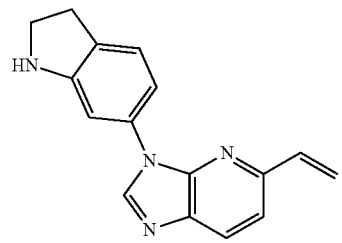

Intermediate 16.1: 3-(2,3-dihydro-1H-indol-6-yl)-5-vinyl-3H-imidazo[4,5-b]pyridine (Scheme 12)

A mixture of tert-butyl 6-(5-vinyl-3H-imidazo[4,5-b]pyridin-3-yl)indoline-1-carboxylate (4.90 g, 13.52 mmol) (Intermediate 15.3), 4 M HCl in 1,4-dioxane (200 ml), 2-propanol (30 ml), and dioxane (50 ml) is stirred for 1 h at ambient temperature. The mixture is concentrated to dryness to furnish 4.00 g (99% yield) of the monohydrochloride salt of the corresponding free amine. HPLC (over 10 min 10-85% MeCN/100 mM aq. NaOAc): 99% purity, $t_R$ 7.06 min ($t_{R(SM)}$ 9.78 min). MS (ESI) m/z ($C_{16}H_{14}N_4$) 263.3 (M+1, 100) Finnegan LCQ.

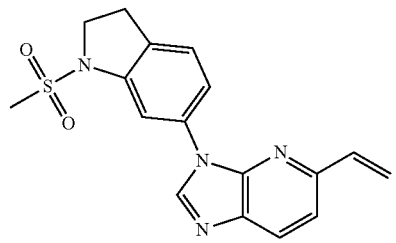

Intermediate 16.2: 3-[1-(methylsulfonyl)-2,3-dihydro-1H-indol-6-yl]-5-vinyl-3H-imidazo[4,5-b]pyridine (Scheme 12)

A solution of 3-(2,3-dihydro-1H-indol-6-yl)-5-vinyl-3H-imidazo[4,5-b]pyridine (Intermediate 16.1) (1.10 g, 4.19 mmol), methanesulfonyl chloride (0.65 ml, 8.39 mmol), and triethylamine (3.49 ml, 25.16 mmol) in dichloromethane (50 ml) is stirred for 15 min at ambient temperature. The mixture is successively extracted with saturated aqueous ammonium chloride and saturated aqueous sodium bicarbonate. The organic layer is dried over sodium sulfate and concentrated in vacuo to render 1.40 g (98%) of the respective sulfonamide. HPLC (over 10 min 10-85% MeCN/100 mM aq. NaOAc): 99% purity, $t_R$ 7.03 min ($t_{R(SM)}$ 7.06 min). MS (ESI) m/z ($C_{17}H_{16}N_4O_2S$) 341.0 (M+1, 100) Finnegan LCQ.

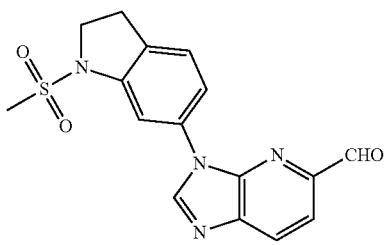

Intermediate 16.3: 3-[1-(methylsulfonyl)-2,3-dihydro-1H-indol-6-yl]-3H-imidazo[4,5-b]pyridine-5-carbaldehyde (Scheme 13)

The title compound is obtained from 3-[1-(methylsulfonyl)-2,3-dihydro-1H-indol-6-yl]-5-vinyl-3H-imidazo[4,5-b]pyridine (Intermediate 16.2) in 99% yield following general procedure V. HPLC (over 10 min 10-85% MeCN/100 mM aq. NaOAc): 93% purity, $t_R$ 6.09 min ($t_{R(SM)}$ 7.03 min). MS (ESI) m/z ($C_{16}H_{14}N_4O_3S$) 343.0 (M+1, 100) Finnegan LCQ.

Example 1

(5Z)-5-{[4-(1-piperidinyl)pyrido[3,2-d]pyrimidin-6-yl]methylene}-1,3-thiazolidine-2,4-dione potassium salt (1) (Scheme 2)

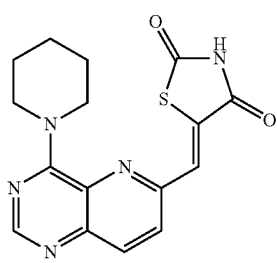

(1)

A mixture of 2,4-thiazolidinedione (3.4 g; 29.1 mmol; 1.80 eq.), pyrrolidine (269.80 µL; 3.2 mmol; 0.2 eq.) in MeOH (50 mL) was heated at 70° C. A solution of 4-(1-piperidinyl)pyrido[3,2-d]pyrimidine-6-carbaldehyde (Intermediate 1.7) (3.9 g; 16.2 mmol; 1 eq.) in MeOH (50 mL) was slowly added over 1.5 hour at 70° C. After 2 h under reflux after the addition, the reaction was complete. A precipitate was formed. The hot reaction mixture was filtered and the solid was washed with cold MeOH to give (5Z)-5-{[4-(1-piperidinyl)pyrido[3,2-d]pyrimidin-6-yl]methylene}-1,3-thiazolidine-2,4-dione (1) (2.70 g; 48%) as an orange powder in 98% HPLC purity.

(5Z)-5-{[4-(1-piperidinyl)pyrido[3,2-d]pyrimidin-6-yl]methylene}-1,3-thiazolidine-2,4-dione (2.7 g; 8.1 mmol; 1 eq.) was suspended in THF (80 mL) and water (80 mL). Potassium hydroxide (16.2 mL; 0.50 M; 8.1 mmol; 1 eq.) was added and the solution was filtered through cotton and rinsed with water. After lyophilization, (5Z)-5-{[4-(1-piperidinyl)pyrido[3,2-d]pyrimidin-6-yl]methylene}-1,3-thiazolidine-2,4-dione potassium salt (1) (3.06 g, 98%) was isolated as a yellow solid in 99.36% HPLC purity. Amount: 3.06 g; Yield: 99%; Melting point: 319° C.; Formula: $C_{16}H_{14}O_2SN_5.K$; IR (neat) ν 3355.1, 2932.9, 2852.7, 1674.1, 1519.6 cm$^{-1}$; 1H NMR (DMSO-d6) δ 1.68 (sl, 6H), 4.34 (sl, 4H), 7.44 (s, 1H), 7.93 (d, J=9 Hz, 1H), 8.04 (d, J=9 Hz, 1H), 8.45 (s, 1H); HPLC (H$_2$O TFA 0.1%-ACN TFA 0.05%): Rt (min); Area %=2.07; 99.10; LC-MS: M/Z ESI: Rt (min) 1.36; 342.04 (M+1); 340.08 (M−1).

Example 2

(5Z)-5-{[4-(4-fluoro-1-piperidinyl)pyrido[3,2-d]pyrimidin-6-yl]methylene}-1,3-thiazolidine-2,4-dione potassium salt (2) (Scheme 2)

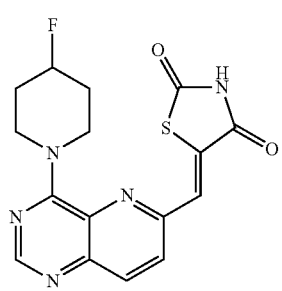

(2)

The title compound was obtained following the general procedure described for Example 1, using Intermediate 2.1, 4-(4-fluoro-piperidin-1-yl)-pyrido[3,2-d]pyrimidine-6-carbaldehyde. After lyophilization, (5Z)-5-{[4-(4-fluoro-1-piperidinyl)pyrido[3,2-d]pyrimidin-6-yl]methylene}-1,3-thiazolidine-2,4-dione potassium salt (2) was isolated as an orange solid in 98.8% HPLC purity; Formula: $C_{16}H_{13}FO_2SN_5.K$; 1H NMR (DMSO-d6) δ 1.86 (m, 2H), 2.07 (m, 2H), 4.39 (m, 4H), 5.00 (m, 1H), 7.44 (s, 1H), 7.97 (d, J=9 Hz, 1H), 8.07 (d, J=9 Hz, 1H), 8.50 (s, 1H); HPLC (H$_2$O TFA 0.1%-ACN TFA 0.05%): Rt (min); Area %=1.92; 98.76; LC-MS: M/Z ESI: Rt (min) 1.27; 360.07 (M+1); 358.07 (M−1).

Example 3

(5Z)-5-({4-[4-(trifluoromethyl)-1-piperidinyl]pyrido[3,2-d]pyrimidin-6-yl}methylene)-1,3-thiazolidine-2,4-dione potassium salt (3) (Scheme 2)

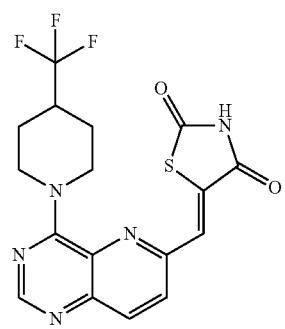

(3)

The title compound was obtained following the general procedure described for Example 1, using Intermediate 3.1, 4-(4-(trifluoromethyl)-piperidin-1-yl)-pyrido[3,2-d]pyrimidine-6-carbaldehyde. After lyophilisation, (5Z)-5-({4-[4-(trifluoromethyl)-1-piperidinyl]pyrido[3,2-d]pyrimidin-6- yl}methylene)-1,3-thiazolidine-2,4-dione potassium salt (3) was isolated as an orange solid in 99.5% HPLC purity; Formula: $C_{17}H_{13}O_2SF_3N_5.K$; 1H NMR (DMSO-d6) δ 1.39 (m, 2H), 1.76 (m, 2H), 2.59 (m, 1H), 3.05 (m, 2H), 5.44 (m, 2H), 7.24 (s, 1H), 7.76 (d, J=9 Hz, 1H), 7.87 (d, J=9 Hz, 1H), 8.30 (s, 1H); HPLC (H$_2$O TFA 0.1%-ACN TFA 0.05%): Rt (min); Area %=244; 88.47: LC-MS: M/Z ESI: Rt (min) 1.55; 410.09 (M+1); 408.09 (M−1).

Example 4

5-Pyrido[2,3-b]pyrazin-6-ylmethylene-thiazolidine-2,4-dione (4) (Scheme 3)

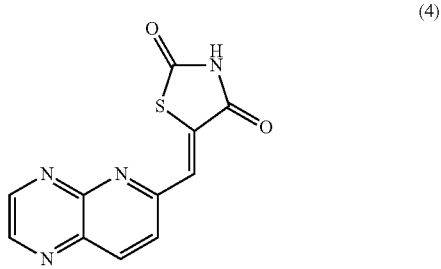

(4)

Pyrido[2,3-b]pyrazine-6-carbaldehyde (Intermediate 4.4) (300 mg, 1.89 mmol, 1 eq.), 2,5-thiazolidinedione (397 mg, 3.4 mmol, 1.8 eq.) and pyrrolidine (0.03 mL, 0.38 mmol, 0.2 eq.) were heated in methanol (10 mL) for 3 hours at 65° C. When reaction was finished, water (3 mL) was added and corresponding brown precipitate filtered off, washed with methanol, water and then diethyl ether to give 200 mg of the pure expected compound (4). From the free base (200 mg, 0.78 mmol, 1 eq.), a potassium salt was synthesized using KOH (1M, V=0.78 mL, 1 eq.) to give 231 mg of the corresponding potassium salt. Amount: 231 mg (potassium salt); Yield: 41%; Formula: C11H6O2SN4.K; HPLC Purity: 98.7%; HPLC (H$_2$O TFA 0.1%-ACN TFA 0.05%): Rt (min); Area %=1.89 min; 98.7%; 1H NMR (DMSO-d6) δ 9.09 (s, 1H), 8.95 (s, 1H), 8.46 (d, 1H, J=8 Hz), 8.02 (d, 1H, J=8 Hz), 7.52 (s, 1H); LC-MS: M/Z ESI: Rt (min) 0.76 min, 259.07 (M+1).

Example 5

5-Furo[3,2-b]pyridin-5-ylmethylene-thiazolidine-2,4-dione (5) (Scheme 4)

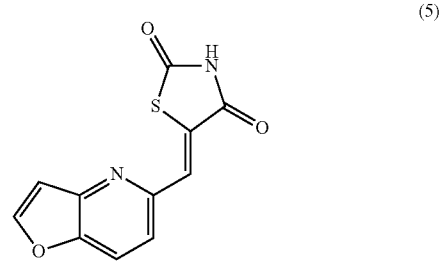

(5)

A solution of 2-(trimethylsilyl)furo[3,2-b]pyridine-5-carbaldehyde (Intermediate 5.2) (130 mg; 0.59 mmol; 1 eq.), 2,4-thiazolidinedione (125 mg; 1.07 mmol; 1.8 eq.) and beta-alanine (95 mg; 1.07 mmol; 1.8 eq.) in acetic acid (2 mL) was heated at 100° C. for 7 h. Water was added and the precipitate was filtered and washed with Et$_2$O to afford a solid (purity: 98.14%, yield: 25%). Then (5Z)-5-{[2-(trimethylsilyl)furo[3,2-b]pyridin-5-yl]methylene}-1,3-thiazolidine-2,4-dione (41 mg; 0.13 mmol; 1 eq.) was dissolved in MeOH (5 mL). NaOH (5N aqueous) was added (150.00 μl). The solution was stirred at rt. After 24 hours the reaction was complete. AcOH (1mL) was added and the solution was concentrated in vacuum. Water was added and the precipitate was filtered, washed with water, Et$_2$O and MeOH to afford a solid (5). From the free base (24 mg, 0.097 mmol, 1 eq.), a potassium salt was synthesized using KOH (1M, V=0.097 mL, 1 eq.) affording 24 mg of the corresponding potassium salt. Amount: 24 mg (potassium salt); Yield: 75%; Formula: C11H6N2O3S.K; HPLC Purity: 98.03%; HPLC (H$_2$O TFA 0.1%-ACN TFA 0.05%): Rt (min); Area %=2.96 min; 98.03%; 1H NMR (DMSO-d6) δ 8.30 (s, 1H), 8.00 (d, 1H, J=9 Hz), 7.51 (d, 1H, J=9 Hz), 7.37 (s, 1H), 7.13 (s, 1H); LC-MS: M/Z ESI: Rt (min) 1.31 min, 246.95 (M+1).

Example 6

5-[4-(4-Fluoro-piperidin-1-yl)-pyrido[3,2-d]pyrimidin-6-ylmethylene]-2-thioxo-thiazolidin-4-one (Scheme 2)

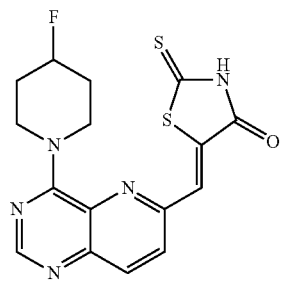

(6)

The title compound was obtained following the general procedure described for Example 1, using rhodanine (instead of thiazolidinedione) and Intermediate 2.1, 4-(4-fluoro-piperidin-1-yl)-pyrido[3,2-d]pyrimidine-6-carbaldehyde. After lyophilization, 5-[4-(4-Fluoro-piperidin-1-yl)-pyrido[3,2-d]pyrimidin-6-ylmethylene]-2-thioxo-thiazolidin-4-one potassium salt (6) was isolated as an orange solid in 95.5% HPLC purity; Formula: $C_{16}H_{13}FOS_2N_5.K$; 1H NMR (DMSO-d6) δ 1.89 (m, 4H), 4.42 (m, 4H), 5.00 (m, 1H), 7.29 (s, 1H), 8.07 (d, J=9 Hz, 2H), 8.52 (s, 1H); HPLC (H$_2$O TFA 0.1%-ACN TFA 0.05%): Rt (min); Area %=2.37 min; 95.54%; LC-MS: M/Z ESI: Rt (min) 1.38 min; 376.11 (M+1); 374.11 (M−1).

Example 7

(5Z)-5-[(3-phenyl-3H-imidazo[4,5-b]pyridin-5-yl)methylene]-1,3-thiazolidine-2,4-dione (Scheme 5)

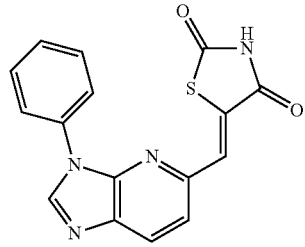

(7)

The title compound was obtained from 3-phenyl-3H-imidazo[4,5-b]pyridine-5-carbaldehyde in 55% yield following general procedure described for Example 1. HPLC (over 10 min 10-85% MeCN/100 mM aq. NaOAc): 96% purity, $t_R$ 4.95 min. MS (ESI) m/z ($C_{16}H_{10}N_4O_2S$) 361.2 (M+K$^+$, 100). $^1$H-NMR (JEOL 400 MHz, DMSO-d$_6$): δ 8.97 (s, 1H), 8.23 (d, 1H), 8.13 (d, 2H), 7.70-7.45 (m, 5H).

Example 8

Preparation of (5Z)-5-{[3-(3,5-dimethoxyphenyl)-3H-imidazo[4,5-b]pyridin-5-yl]methylene}-1,3-thiazolidine-2,4-dione (Scheme 5)

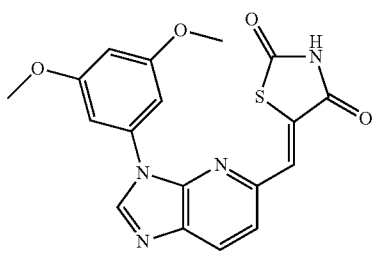

(8)

The title compound is obtained from 3-(3,5-dimethoxyphenyl)-3H-imidazo[4,5-b]pyridine-5-carbaldehyde in 85% yield following general procedure VI. HPLC (over 10 min 10-85% MeCN/100 mM aq. NaOAc): 96% purity, $t_R$ 5.12 min ($t_{R(SM)}$ 7.26 min). $^1$H-NMR (JEOL 400 MHz, DMSO-d$_6$): δ 8.90 (s, 1H), 8.16 (d, 1H), 7.58 (d, 1H), 7.41 (s, 1H), 7.24 (s, 2H), 6.60 (s, 1H), 3.87 (s, 6H).

Example 9

Tert-butyl 5-{5-[(Z)-(2,4-dioxo-1,3-thiazolidin-5-ylidene)methyl]-3H-imidazo[4,5-b]pyridin-3-yl}indoline-1-carboxylate (Scheme 5)

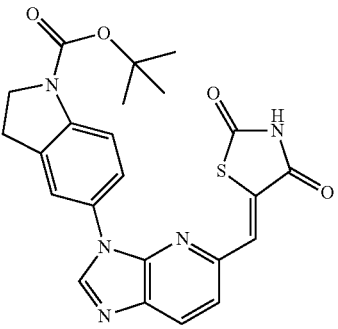

(9)

The title compound is obtained from tert-butyl 5-(5-formyl-3H-imidazo[4,5-b]pyridin-3-yl)indoline-1-carboxylate in 65% yield following general procedure VI. HPLC (over 10 min 10-85% MeCN/0.1% TFA/H$_2$O): 94% purity, $t_R$ 6.50 min ($t_{R(SM)}$ 7.31 min). $^1$H-NMR (JEOL 400 MHz, DMSO-d$_6$) δ 8.89 (s, 1H), 8.17 (s, 1H), 8.12 (d, 1H), 7.92 (br s, 0.5H), 7.88 (s, 1H), 7.59 (br s, 0.5H), 7.58 (d, 1H), 7.28 (d, 1H), 4.06 (br t, 2H), 3.24 (t, 2H), 1.54 (s, 9H) ppm. MS (ESI) m/z ($C_{23}H_{20}N_5O_4S$) 464.1 (M+1, 100), 408.1 (60) Finnegan LCQ.

Example 10

(5Z)-5-{[3-(2,3-dihydro-1H-indol-5-yl)-3H-imidazo[4,5-b]pyridin-5-yl]methylene}-1,3-thiazolidine-2,4-dione (Scheme 5)

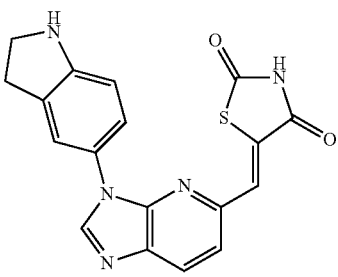

(10)

A mixture of tert-butyl 5-{5-[(Z)-(2,4-dioxo-1,3-thiazolidin-5-ylidene)methyl]-3H-imidazo[4,5-b]pyridin-3-yl}indoline-1-carboxylate (35.0 mg, 75.5 mmol) (Example 9), 4 M HCl in 1,4-dioxane (3 ml), and 2-propanol (1 ml) is stirred for 1.5 h at ambient temperature. The mixture is concentrated to dryness, washed with water, and dried in vacuo to furnish 27.3 mg (89% yield) of the monohydrochloride salt of the corresponding free amine. HPLC (over 10 min 10-85% MeCN/100 mM aq. NaOAc): 98% purity, $t_R$ 4.44 min ($t_{R(SM)}$ 6.23 min). $^1$H-NMR (JEOL 400 MHz, DMSO-d$_6$) δ 9.03 (s, 1H), 8.33 (d, 1H), 8.01 (s, 1H), 7.96 (s, 1H), 7.91 (d, 1H), 7.75 (d, 1H), 7.34 (d, 1H), 3.97 (br s, 4H), 3.74 (t, 2H), 3.22 (t, 2H) ppm. MS (ESI) m/z ($C_{18}H_{13}N_5O_2S$) 364.1 (M+1, 100), 329.2 (21) Finnegan LCQ.

Example 11

(5Z)-5-{[3-(1-acetyl-2,3-dihydro-1H-indol-5-yl)-3H-imidazo[4,5-b]pyridin-5-yl]methylene}-1,3-thiazolidine-2,4-dione (Scheme 5)

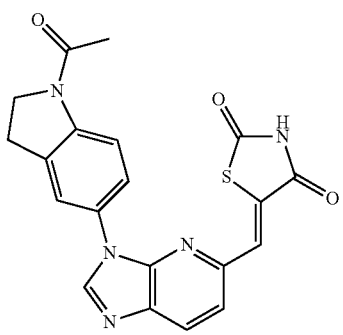

(11)

The title compound is obtained from 3-(1-acetyl-2,3-dihydro-1H-indol-5-yl)-3H-imidazo[4,5-b]pyridine-5-carbaldehyde (intermediate 10.3) in 55% yield following general procedure VI. HPLC (over 10 min 10-85% MeCN/100 mM aq. NaOAc): 99% purity, $t_R$ 4.46 min ($t_{R(SM)}$ 5.38 min). $^1$H-NMR (JEOL 400 MHz, DMSO-$d_6$, 65° C.) δ 12.23 (br s, 1H), 8.89 (s, 1H), 8.27 (d, 1H), 8.22 (br s, 1H), 7.93 (s, 1H), 7.90 (s, 1H), 7.83 (d, 1H), 7.70 (d, 1H), 4.23 (t, 2H), 3.29 (t, 2H), 2.23 (s, 3H) ppm. MS (ESI) m/z ($C_{20}H_{15}N_5O_3S$) 406.3 (M+1, 100) Finnegan LCQ.

Example 12

(5Z)-5-[(3-{1-[4-(dimethylamino)butanoyl]-2,3-dihydro-1H-indol-5-yl}-3H-imidazo[4,5-b]pyridin-5-yl)methylene]-1,3-thiazolidine-2,4-dione

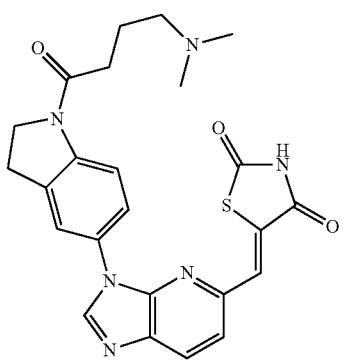

(12)

The title compound is obtained from 3-{1-[4-(Dimethylamino)butanoyl]-2,3-dihydro-1H-indol-5-yl}-3H-imidazo[4,5-b]pyridine-5-carbaldehyde (intermediate 11.2) in 78% yield following general procedure VI. HPLC (over 10 min 10-85% MeCN/100 mM aq. NaOAc): 98% purity, $t_R$ 4.14 min ($t_{R(SM)}$ 5.02 min). $^1$H-NMR (JEOL 400 MHz, DMSO-$d_6$) δ 8.94 (s, 1H), 8.28 (d, 1H), 8.22 (d, 1H), 7.98 (s, 1H), 7.76 (br s, 3H), 4.23 (t, 2 H), 3.45 (br s, mH), 3.31 (t, 2H), 2.71 (t, 2H), 2.59 (t, 2H), 2.52 (s, 6H), 1.88 (m, 2H) ppm. MS (ESI) m/z ($C_{24}H_{24}N_6O_3S$) 477.1 (M+1, 100), 432.2 (49), 272.3 (19), 260.4 (21) Finnegan LCQ.

Example 13

(5Z)-5-({3-[1-(methylsulfonyl)-2,3-dihydro-1H-indol-5-yl]-3H-imidazo[4,5-b]pyridin-5-yl}methylene)-1,3-thiazolidine-2,4-dione (Scheme 5)

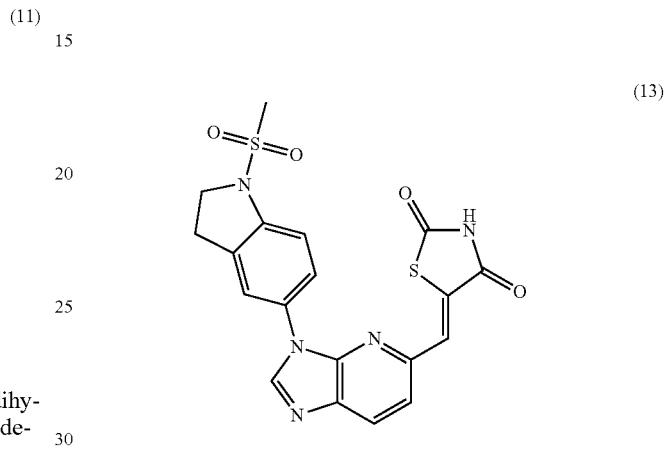

(13)

The title compound is obtained from 3-[1-(methylsulfonyl)-2,3-dihydro-1H-indol-5-yl]-3H-imidazo[4,5-b]pyridine-5-carbaldehyde (intermediate 12.2) in 62% yield following general procedure VI. HPLC (over 10 min 10-85% MeCN/100 mM aq. NaOAc): 99% purity, $t_R$ 4.80 min ($t_{R(SM)}$ 6.13 min). $^1$H-NMR (JEOL 400 MHz, DMSO-$d_6$) δ 8.97 (s, 1H), 8.32 (d, 1H), 7.96 (s, 2H), 7.87 (d, 1H), 7.74 (d, 1H), 7.45 (d, 1H), 4.09 (t, 2H), 3.28 (t, 2H), 3.10 (s, 3H) ppm. MS (ESI) m/z ($C_{19}H_{15}N_5O_4S_2$) 442.1 (M+1, 100), 363.0 (27), 291.3 (22).

Example 14

Preparation of (5Z)-5-[(3-{1-[(chloromethyl)sulfonyl]-2,3-dihydro-1H-indol-5-yl}-3H-imidazo[4,5-b]pyridin-5-yl)methylene]-1,3-thiazolidine-2,4-dione (Scheme 5)

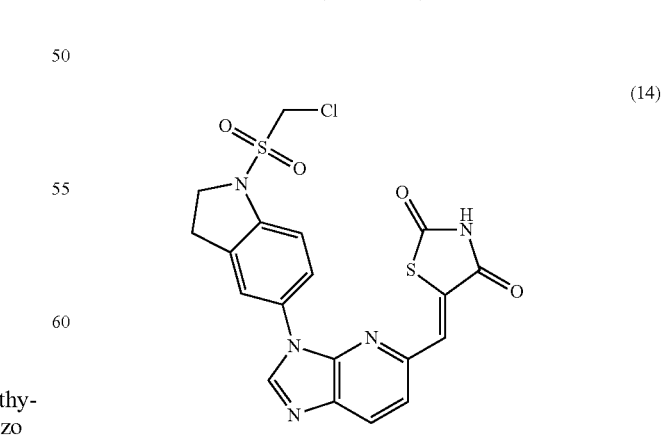

(14)

The title compound is obtained from 3-{1-[(chloromethyl)sulfonyl]-2,3-dihydro-1H-indol-5-yl}-3H-imidazo[4,5-b]

pyridine-5-carbaldehyde (intermediate 13.2) in 60% yield following general procedure VI. HPLC (over 10 min 10-85% MeCN/100 mM aq. NaOAc): 99% purity, $t_R$ 5.37 min ($t_{R(SM)}$ 7.03 min). $^1$H-NMR (JEOL 400 MHz, DMSO-$d_6$) δ 8.92 (s, 1H), 8.31 (d, 1H), 7.98 (d, 2H), 7.88 (d, 1H), 7.75 (d, 1H), 7.52 (d, 1H), 5.38 (s, 2H), 4.22 (t, 2H), 3.30 (t, 2H) ppm. MS (ESI) m/z ($C_{19}H_{14}ClN_5O_4S_2$) 477.0 (M+1, 100) Finnegan LCQ.

Example 15

(5Z)-5-[(3-{1-[(3-morpholin-4-ylpropyl)sulfonyl]-2,3-dihydro-1H-indol-5-yl}-3H-imidazo[4,5-b]pyridin-5-yl)methylene]-1,3-thiazolidine-2,4-dione (Scheme 5)

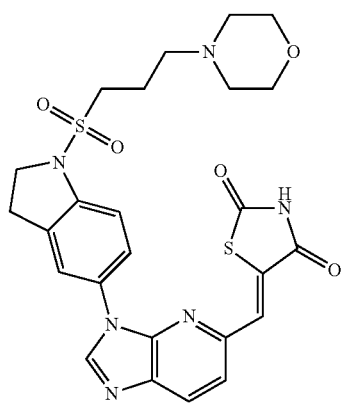

(15)

The title compound is obtained from 3-{1-[(3-morpholin-4-ylpropyl)sulfonyl]-2,3-dihydro-1H-indol-5-yl}-3H-imidazo[4,5-b]pyridine-5-carbaldehyde in 39% yield following general procedure VI. HPLC (over 10 min 10-85% MeCN/ 100 mM aq. NaOAc): $t_R$ 5.50 min ($t_{R(SM)}$ 7.55 min). $^1$H-NMR (JEOL 400 MHz, DMSO-$d_6$) δ 8.93 (s, 1H), 8.22 (s, 1H), 8.20 (s, 1H), 7.85 (d, 1H), 7.66 (d, 1H), 7.56 (s, 1H), 7.42 (d, 1H), 4.13 (t, 2H), 3.74 (m, 2H), 3.50-3.20 (m, 12H), 2.18 (m, 2H) ppm. MS (ESI) m/z ($C_{23}H_{27}N_5O_3S$) 454.0 (M, 10) Finnegan LCQ.

Example 16

Tert-butyl 6-{5-[(Z)-(2,4-dioxo-1,3-thiazolidin-5-ylidene)methyl]-3H-imidazo[4,5-b]pyridin-3-yl}indoline-1-carboxylate (Scheme 5)

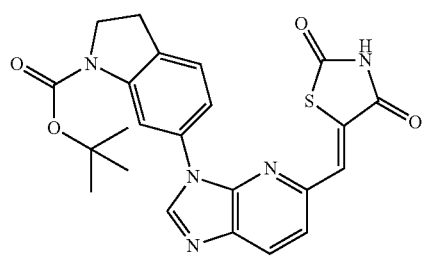

(16)

The title compound is obtained from tert-butyl 6-(5-formyl-3H-imidazo[4,5-b]pyridin-3-yl)indoline-1-carboxylate in 22% yield following general procedure VI. HPLC (over 10 min 10-85% MeCN/100 mM aq. NaOAc): 99% purity, $t_R$ 6.49 min ($t_{R(SM)}$ 8.61 min). $^1$H-NMR (JEOL 400 MHz, DMSO-$d_6$) δ 8.87 (s, 1H), 8.24 (d, 1H), 8.02 (br d, 1H), 7.74 (d, 1H), 7.72 (s, 1H), 7.50 (br s, 1H), 7.41 (d, 1H), 4.05 (t, 2H), 3.20 (t, 2 H), 1.45 (s, 9H), ppm. MS (ESI) m/z ($C_{23}H_{20}N_5O_4S$) 464.0 (M+1, 100), 408.1 (42) Finnegan LCQ.

Example 17

(5Z)-5-({3-[1-(methylsulfonyl)-2,3-dihydro-1H-indol-6-yl]-3H-imidazo[4,5-b]pyridin-5-yl}methylene)-1,3-thiazolidine-2,4-dione (Scheme 5)

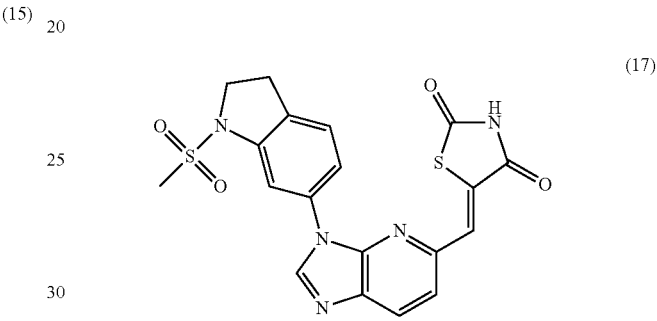

(17)

The title compound is obtained from 3-[1-(methylsulfonyl)-2,3-dihydro-1H-indol-6-yl]-3H-imidazo[4,5-b]pyridine-5-carbaldehyde in 29% yield following general procedure VI. HPLC (over 10 min 10-85% MeCN/100 mM aq. NaOAc): 99% purity, $t_R$ 4.68 min ($t_{R(SM)}$ 6.09 min). $^1$H-NMR (JEOL 400 MHz, DMSO-$d_6$) δ 8.87 (s, 1H), 8.17 (d, 1H), 7.82 (d, 1H), 7.65-7.50 (m, 3H), 7.42 (s, 1H), 4.09 (t, 2H), 3.24 (t, 2H), 3.15 (s, 3H) ppm. MS (ESI) m/z ($C_{19}H_{15}N_5O_4S_2$) 442.0 (M+1, 100), 362.8 (21) Finnegan LCQ.

Example 18

Biological Assays

The compounds of the present invention may be subjected to the following assays:
a) High Throughput PI3K Lipid Kinase Assay (Binding Assay):
The efficacy of compounds of the invention in inhibiting the PI3K induced-lipid phosphorylation may be tested in the following binding assay.

The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 384 wells MTP containing 5 μl of the test compound of Formula (I) (solubilized in 6% DMSO; to yield a concentration of 100, 30, 10, 3, 1, 0.3, 0.1, 0.03, 0.01, 0.001 μM of the test compound), the following assay components are added.

1) 5 µl (58 ng) of Human recombinant GST-PI3Kγ (in Hepes 40 mM, pH 7.4, DTT 1 mM and ethylenglycol 5%) 2) 10 µl of lipid micelles and 3) 10 µl of Kinase buffer ([$^{33}$P]γ-ATP 45 µM/60 nCi, MgCl$_2$ 30 mM, DTT 1 mM, β-Glycerophosphate 1 mM, Na$_3$VO$_4$ 100 µM, Na Cholate 0.3%, in Hepes 40 mM, pH 7.4). After incubation at room temperature for 180 minutes, with gentle agitation, the reaction is stopped by addition of 60 µl of a solution containing 100 µg of neomycin-coated PVT SPA beads in PBS containing ATP 10 mM and EDTA 5 mM. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in Table I below refer to the IC$_{50}$ (nM) with respect to PI3Kγ, i.e. the amount necessary to achieve 50% inhibition of said target. Said values show a considerable inhibitory potency of thiazole compounds with regard to PI3Kγ.

Examples of inhibitory activities for compounds of of the invention are set out in Table I below.

TABLE I

IC$_{50}$ values of thiazole derivatives against PI3Kγ.

| Example No | PI3Kγ IC$_{50}$ (nM) |
|---|---|
| 1 | 4 |
| 3 | 6 |
| 4 | 20 |
| 5 | 35 |
| 6 | 2 |
| 8 | 10 |
| 12 | 7 |
| 15 | 20 | b) Cell Based ELISA to Monitor PI3K Inhibition:

The efficacy of compounds of the invention in inhibiting the PI3K induced Akt/PKB phosphorylation may be tested in the following cell based assay.

Measurement of Akt/PKB phosphorylation in macrophages after stimulation with Complement 5a: Raw 264: Raw 264-7 macrophages (cultured in DMEM-F12 medium containing 10% Fetal Calf serum and antibiotics) are plated at 20'000 cells/well in a 96 MTP 24 h before cell stimulation. Previous to the stimulation with 50 nM of Complement 5a during 5 minutes, Cells are serum starved for 2 h, and pretreated with inhibitors for 20 minutes. After stimulation cells are fixed in 4% formaldehyde for 20 minutes and washed 3 times in PBS containing 1% Triton X-100 (PBS/Triton). Endogenous peroxidase is blocked by a 20 minutes incubation in 0.6% H$_2$O$_2$ and 0.1% Sodium Azide in PBS/Triton and washed 3 times in PBS/Triton. Cells are then blocked by 60 minutes incubation with 10% fetal calf serum in PBS/Triton. Next, phosphorylated Akt/PKB is detected by an overnight incubation at 4° C. with first antibody (anti phospho Serine 473 Akt IHC, Cell Signaling) diluted 800-fold in PBS/Triton, containing 5% bovine serum albumin (BSA). After 3 washes in PBS/Triton, cells are incubated for 60 minutes with a peroxidase conjugated goat-anti-rabbit antibody (1/400 dilution in PBS/Triton, containing 5% BSA), washed 3 times in PBS/Triton, and 2 times in PBS and further incubated in 100 µl of substrate reagent solution (R&D) for 20 minutes. The reaction is stopped by addition of 50 µl of 1 M SO$_4$H$_2$ and absorbance is read at 450 nm.

The values indicated in Table II below reflect the percentage of inhibition of AKT phoshorylation as compared to basal level. Said values show a clear effect of the thiazole compounds on the activation of AKT phosphorylation in macrophages.

Examples of inhibitory activities for compounds of the invention are set out in Table II below.

TABLE II

IC$_{50}$ values of thiazole derivatives in Cell Assay

| Example No | Cell Assay (P-Akt, Elisa) IC$_{50}$ [nM] |
|---|---|
| 1 | <10 |
| 3 | <10 |

Example 19

Thioglycollate-Induced Peritoneal Cavity Cell Recruitment Model

The in vivo efficacy of compounds of the invention in inhibiting the migration of leukocytes upon intraperitoneal challenge of thioglycollate may be tested with the following assay.

Experimental Protocol:

8-10 weeks old female C3H mice were fasted during 18 hours. 15 minutes prior the intraperitoneal injection of thioglycollate (1.5%, 40 ml/kg), the mice were treated orally with Pyridine methylene azolidinones of Formula (I). Control mice received CMC/Tween as vehicle (10 ml/kg). The mice were then sacrificed by CO$_2$ inhalation and the peritoneal cavity was washed two times with 5 ml of ice-cold PBS/1 mM EDTA. The lavages were done 4 hrs or 48 hrs after thioglycollate challenge to evaluate neutrophils or macrophages recruitment, respectively. The white blood cells (neutrophils, lymphocytes or macrophages) were counted using a Beckman Coulter® A$^c$T 5diff™. Dexamethasone was used as reference drug.

Example 20

Preparation of a Pharmaceutical Formulation

Formulation 1—Tablets

A compound of Formula (I) is admixed as a dry powder with a dry gelatin binder in an approximate 1:2 weight ration. A minor amount of magnesium stearate is added as a lubricant. The mixture is formed into 240-270 mg tablets (80-90 mg) of active pyridine methylene azolidinone compound per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active pyridine methylene azolidinone compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and to added with stirring. Sufficient water is then added to produce a total volume of 5 mL.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active pyridine methylene azolidinone compound) in a tablet press.

Formulation 5—Injection

A compound of Formula (I) is dissolved in a buffered sterile saline injectable aqueous medium to a concentration of approximately 5 mg/mL.

The invention claimed is:

1. A pyridine methylene azolidinone compound according to Formula (I)

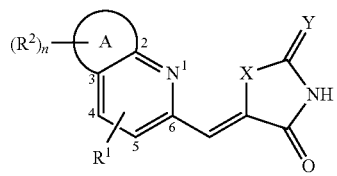

(I)

wherein
- $R^1$ is selected from the group consisting of H, a halogen, a $C_1$-$C_6$-alkyl group, a $C_2$-$C_6$-alkenyl group, a $C_2$-$C_6$-alkynyl group, a $C_1$-$C_6$-alkyl group having an alkoxy substituent, an alkoxycarbonyl group, an acyl group, a sulfonyl group, a sulfanyl group, a sulfinyl group, an alkoxy group, and an amino group;
- $R^2$ is selected from the group consisting of H, a halogen, a $C_1$-$C_6$-alkyl group, a $C_2$-$C_6$-alkenyl group, a $C_2$-$C_6$-alkynyl group, an aryl group, a heteroaryl group, a $C_3$-$C_8$-cycloalkyl group, a $C_3$-$C_8$-heterocycloalkyl group, an aryl $C_1$-$C_6$-alkyl group, a heteroaryl $C_1$-$C_6$-alkyl group, a $C_3$-$C_8$-cycloalkyl $C_1$-$C_6$-alkyl group, a $C_3$-$C_8$-heterocycloalkyl $C_1$-$C_6$-alkyl group, a $C_1$-$C_6$-alkyl alkoxy group, an alkoxycarbonyl group, an acyl group, a sulfonyl group, a sulfanyl group, a sulfinyl group, an alkoxy group and an amino group;
- X is selected from the group consisting of S, NH and O;
- Y is selected from the group consisting of O, S and $NR^3$, wherein $R^3$ is selected from the group consisting of H, a $C_1$-$C_6$-alkoxy group, a substituted $C_1$-$C_6$-alkoxy group, a $C_1$-$C_6$-alkyl group, a substituted $C_1$-$C_6$-alkyl group, a $C_2$-$C_6$-alkenyl group, a substituted $C_2$-$C_6$-alkenyl group, a $C_2$-$C_6$-alkynyl group, a substituted $C_2$-$C_6$-alkynyl group, a $C_1$-$C_6$-alkyl aryl group, a substituted $C_1$-$C_6$-alkyl aryl group, a cyano group, a sulfonyl group, and a substituted sulfonyl group;

A together with the pyridine ring forms a group represented by formula (Ic)

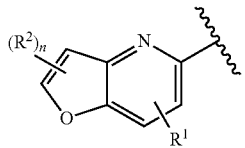

(Ic)

and
n is 1 or 2;
or a pharmaceutically acceptable salt thereof.

2. A pyridine methylene azolidinone compound according to claim 1, wherein $R^1$ is H.

3. A pyridine methylene azolidinone compound according to claim 1, wherein n is 1 or 2 and at least one $R^2$ is H.

4. A pyridine methylene azolidinone compound according to claim 1, wherein n is 1 and $R^2$ is H.

5. A pyridine methylene azolidinone compound according to claim 1, wherein n is 2 and each $R^2$ is H.

6. A pyridine methylene azolidinone compound according to claim 1, wherein at least one $R^2$ is $C_3$-$C_8$-heterocycloalkyl.

7. A pyridine methylene azolidinone compound according to claim 1, wherein at least one $R^2$ is an aryl group or a heteroaryl group.

8. A pyridine methylene azolidinone compound according to claim 1, wherein X is S.

9. A pyridine methylene azolidinone compound according to claim 1, wherein Y is O or S.

10. A pyridine methylene azolidinone compound according to claim 1, wherein Y is O.

11. A pyridine methylene azolidinone compound according to claim 1, wherein Y is S.

12. A pyridine methylene azolidinone compound according to claim 1, wherein n is 1.

13. A pyridine methylene azolidinone compound according to claim 1, wherein
$R^1$ is H;
X is S; and
Y is O.

14. A pyridine methylene azolidinone compound according to claim 1, which is 5-Furo[3,2-b]pyridin-5-ylmethylene-thiazolidine-2,4-dione.

15. A pharmaceutical composition comprising a pyridine methylene azolidinone compound according to claim 1 and a pharmaceutically acceptable carrier, diluent or excipient thereof.

* * * * *